United States Patent
Noh et al.

(10) Patent No.: US 10,411,199 B2
(45) Date of Patent: Sep. 10, 2019

(54) ORGANOMETALLIC COMPLEXES, AND ORGANIC ELECTROLUMINESCENT DEVICE AND DISPLAY USING THE SAME

(71) Applicants: SAMSUNG ELECTRONICS CO., LTD., Suwon-si, Gyeonggi-do (KR); CHEIL INDUSTRIES INC., Gumi-si, Gyeongsangbuk-do (KR)

(72) Inventors: Chang Ho Noh, Suwon-si (KR); O Hyun Kwon, Yongin-si (KR); Ragini Das Rupasree, Suwon-si (KR); Dmitry Kravchuk, Hwaseong-si (KR); Hyeon Ho Choi, Seoul (KR)

(73) Assignees: SAMSUNG ELECTRONICS CO., LTD., Gyeonggi-Do (KR); CHEIL INDUSTRIES INC., Gyeongsangbuk-Do (KR)

( * ) Notice: Subject to any disclaimer, the term of this patent is extended or adjusted under 35 U.S.C. 154(b) by 1215 days.

(21) Appl. No.: 13/921,646

(22) Filed: Jun. 19, 2013

(65) Prior Publication Data

US 2014/0158998 A1    Jun. 12, 2014

(30) Foreign Application Priority Data

Dec. 12, 2012    (KR) .................. 10-2012-0144603

(51) Int. Cl.
*H01L 51/00* (2006.01)
*C09K 11/06* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS 7,585,573 B2    9/2009 Lee et al.
7,776,458 B2    8/2010 Ragini et al.
(Continued)

FOREIGN PATENT DOCUMENTS

EP    2562229 A1    2/2013
JP    2007-099961 A    4/2007
(Continued)

OTHER PUBLICATIONS

Machine English translation of Nishizeki et al. (JP 2009-102533 A). Nov. 21, 2016.*
(Continued)

*Primary Examiner* — Jay Yang
(74) *Attorney, Agent, or Firm* — Cantor Colburn LLP

(57) ABSTRACT

An organometallic complex represented by Chemical Formula 1:

Chemical Formula 1

(Continued)

wherein M, CyN, CyC, $X^1$, $X^2$, $R_1$ to $R^4$, R' and n are described in the specification.

16 Claims, 3 Drawing Sheets

(51) Int. Cl.
   *H05B 33/14* (2006.01)
   *C07F 15/00* (2006.01)

(52) U.S. Cl.
   CPC ...... *H05B 33/14* (2013.01); *C09K 2211/1007* (2013.01); *C09K 2211/1029* (2013.01); *C09K 2211/1044* (2013.01); *C09K 2211/185* (2013.01); *H01L 51/0067* (2013.01); *H01L 51/0072* (2013.01); *H01L 51/0094* (2013.01)

(56) References Cited

U.S. PATENT DOCUMENTS

| | | |
|---|---|---|
| 8,142,909 B2 | 3/2012 | Beers et al. |
| 8,945,725 B2 | 2/2015 | Takizawa et al. |
| 2002/0048689 A1 | 4/2002 | Igarashi et al. |
| 2002/0064681 A1 | 5/2002 | Takiguchi et al. |
| 2002/0182441 A1 | 12/2002 | Lamansky et al. |
| 2004/0053071 A1* | 3/2004 | Igarashi .............. C07F 15/0033 428/690 |
| 2006/0258043 A1 | 11/2006 | Bold et al. |
| 2007/0020479 A1 | 1/2007 | Uetani et al. |
| 2008/0103308 A1* | 5/2008 | Ragini ................ C07F 15/0033 546/5 |
| 2009/0200920 A1 | 8/2009 | Jin et al. |
| 2011/0025398 A1 | 2/2011 | Chan |
| 2011/0155954 A1 | 6/2011 | Yersin et al. |
| 2012/0025178 A1 | 2/2012 | Inoue et al. |
| 2012/0097932 A1 | 4/2012 | Kim et al. |
| 2012/0097936 A1 | 4/2012 | Ahn et al. |
| 2012/0097937 A1 | 4/2012 | Iwakuma et al. |
| 2012/0097998 A1 | 4/2012 | Pieh et al. |
| 2012/0098413 A1 | 4/2012 | Lin et al. |
| 2012/0104379 A1 | 5/2012 | Kawakami et al. |
| 2012/0104941 A1 | 5/2012 | Jung et al. |
| 2012/0104957 A1 | 5/2012 | Yano et al. |
| 2012/0115767 A1 | 5/2012 | van Buskirk et al. |
| 2012/0121933 A1 | 5/2012 | Ma et al. |
| 2012/0138917 A1 | 6/2012 | Lee et al. |
| 2012/0138964 A1 | 6/2012 | Hsu |
| 2012/0153324 A1 | 6/2012 | Lin et al. |
| 2012/0159845 A1 | 6/2012 | Alkala |
| 2012/0161111 A1 | 6/2012 | Chiang et al. |
| 2012/0161114 A1 | 6/2012 | Kim et al. |
| 2012/0161612 A1 | 6/2012 | Kim et al. |
| 2015/0243913 A1 | 8/2015 | Takizawa et al. |

FOREIGN PATENT DOCUMENTS

| | | |
|---|---|---|
| JP | 2008-074831 A | 4/2008 |
| JP | 2008-074921 A | 4/2008 |
| JP | 2009001742 A | 1/2009 |
| JP | 2009016719 A | 1/2009 |
| JP | 2009096861 A | 5/2009 |
| JP | 2009102533 A * | 5/2009 |
| JP | 2010120893 A | 6/2010 |
| KR | 1020050053994 A | 6/2005 |
| KR | 1020060006836 A | 1/2006 |
| KR | 1020060011933 A | 2/2006 |
| KR | 1020080066672 A | 7/2008 |
| KR | 20110131200 A | 12/2011 |
| KR | 10-2012-0081076 A | 7/2012 |
| WO | 0215645 A1 | 2/2002 |
| WO | 2004017043 A2 | 2/2004 |
| WO | 2005019373 A2 | 3/2005 |
| WO | 2005123873 A1 | 12/2005 |
| WO | 2008142976 A1 | 11/2008 |
| WO | 2009047993 A1 | 4/2009 |
| WO | 2010086089 A1 | 8/2010 |
| WO | 2010090362 A1 | 8/2010 |
| WO | 2011024986 A1 | 3/2011 |
| WO | 2011025068 A1 | 3/2011 |
| WO | 2012019948 A1 | 2/2012 |
| WO | 2012039241 A1 | 3/2012 |
| WO | 2013094276 A1 | 6/2013 |

OTHER PUBLICATIONS

Ikemizu, et al., "Organic electroluminescent materials, organic electroluminescent devices, display devices, and illumination apparatus," Database CA [Online] Chemical Abstracts Service, Columbus, Ohio, US, Doc No. XP-002710679, May 8, 2013, 3 pages.

Ikemizu, et al., "Organic electroluminescent (EL) element with controlled emission wavelength, high emission efficiency, and long luminescence life and its display and illumination," Database CA [Online] Chemical Abstracts Service, Columbus, Ohio, US, Doc No. XP-002710682, May 8, 2013, 8 pages.

Nishizeki, et al., "Manufacture of imidazophenanthridine compounds for organic electroluminescent devices, display devices, and light emitting devices," Database CA [Online] Chemical Abstracts Service, Columbus, Ohio, US, Doc No. XP-002710678, May 8, 2013, 15 pages.

Nishizeki, et al., "Organic electroluminescent (EL) materials of tetracyclic heterocycle-transition metal complexes, EL devices therefrom, and displays and illumination devices therewith," Database CA [Online] Chemical Abstracts Service, Columbus, Ohio, US, Doc No. XP-002710677, May 8, 2013, 10 pages.

Oshiyama, et al., "Organic electroluminescent device, display device and illuminating device showing high luminous efficiency, low driving voltage and long emission life," Database CA [Online] Chemical Abstracts Service, Columbus, Ohio, US, Doc No. XP-002710680, May 8, 2013, 4 pages.

Partial European Search Report dated Sep. 5, 2013 of the corresponding European Patent Application No. 13172293.6, 13 pages.

Otsu, et al., "Organic electroluminescence element, display device, illuminating device and organic electroluminescence element material," Database CA [Online] Chemical Abstracts Service, Columbus, Ohio, US, Doc No. XP-002710683, May 8, 2013, 3 pages.

Yasukawa, et al., "Organic electroluminescent device showing improved light efficiency, luminescence lifetime, uniform brightness, and suppressed dark spot formation, and its use in display and illumination apparatus," Database CA [Online] Chemical Abstracts Service, Columbus, Ohio, US, Doc No. XP-002710681, May 8, 2013, 4 pages.

C Adachi et al., High-efficiency organic electrophosphorescent devices with tris(2-phenylpyridine)iridium doped into electron-transporting materials, Applied Physics Letters, vol. 77, Aug. 7, 2000, pp. 904-906.

C Adachi et al., High-efficiency red electrophosphorescence devices, Applied Physics Letters, vol. 78, Mar. 12, 2001, pp. 1622-1624.

M.A. Baldo et al., Very high-efficiency green organic light-emitting devices based on electrophosphorescence, Applied Physics Letters, vol. 75, Jul. 5, 1999, pp. 4-6.

M.A. Baldo et al., High efficient phosphorescent emission from organic electroluminescent devices, Nature, Sep. 10, 1998, vol. 395, pp. 151-154.

R.R. Das et al., Electrophosphorescent Light Emitting Devices Using New Iridium(III) Complexes, Mat. Res. Soc. Symp. Proc., vol. 708, 2002, Materials Research Society, pp. 39.1-39.6.

F.O. Garces et al., Synthesis, Structure, Electrochemistry, and Photophysics of Methyl-Substituted Phenylpyridine Ortho-Metalated Iridium(III) Complexes, Inorganic Chemistry, 1988, vol. 27, pp. 3464-3471.

Office Action dated Sep. 8, 2016, issued for Korean Patent Application No. 10-2016-0080858.

* cited by examiner

ORGANOMETALLIC COMPLEXES, AND ORGANIC ELECTROLUMINESCENT DEVICE AND DISPLAY USING THE SAME

CROSS-REFERENCE TO RELATED APPLICATION

This application claims priority to and the benefit of Korean Patent Application No. 10-2012-0144603 filed on Dec. 12, 2012, and all the benefits accruing therefrom under 35 U.S.C. § 119, the content of which is incorporated herein in its entirety by reference.

BACKGROUND

1. Field

An organometallic complex, an organic electroluminescent device, and a display device using the same are disclosed.

2. Description of the Related Art

An organic electroluminescent device is a display element that actively emits light when a current flows into a fluorescent or phosphorescent organic compound thin layer (hereinafter, an organic layer) in such a way that electrons and holes are combined in the organic layer. The organic electroluminescent device usually has light weight, consists of simple parts, has a simple structure for manufacturing, and secures high image quality and a wide viewing angle. In addition, the organic electroluminescent device may perfectly realize high color purity and a motion picture, and has appropriate electrical characteristics of low power consumption and low voltage driving for a portable electronic device.

In general, the organic electroluminescent device includes an anode disposed on a substrate, and a hole transport layer ("HTL"), an emission layer, an electron transport layer ("ETL"), and a cathode sequentially formed on the anode. Herein, the hole transport layer ("HTL"), the emission layer, and the electron transport layer ("ETL") are organic layers formed of an organic compound. The organic electroluminescent device is operated as follows. When a voltage is applied between the anode and the cathode, holes injected from the anode pass through the hole transport layer ("HTL") and move toward the emission layer. On the other hand, electrons pass through the electron transport layer ("ETL") from the cathode and are injected into the emission layer, in which the carriers are recombined and produce exitons. The exitons are radioactively decayed and emit light with a wavelength corresponding to the band gap of a used material.

The emission layer may be formed of a phosphor material using singlet exitons and a phosphorescent material using triplet exitons depending on a light emitting mechanism thereof. The phosphor material or phosphorescent material itself doped on an appropriate host material may be used to form the emission layer. When electrons are excited, singlet and triplet exitons are formed on the host material. Herein, the singlet and triplet exitons are produced in a ratio of about 1:3.

When the phosphor material is used as an emission layer-forming material, an organic electroluminescent device wastes triplet exitons produced from a host material. However, when the phosphorescent material is used as the emission layer-forming material, both singlet and triplet exitons may be used to reach 100% internal quantum efficiency. Accordingly, the phosphorescent material may have higher luminous efficiency than the phosphor material.

On the other hand, when a heavy metal such as Ir, Pt, Rh, and Pd is introduced into an organic molecule, the singlet and triplet exitons are spin-orbitally coupled and mixed due to heavy atom effects, and are thus transferred and effectively become phosphorescent even at room temperature.

As mentioned above, various materials using a transition element compound including a transition element such as iridium, platinum, and the like have been reported as a phosphorescent light emitting material with high efficiency. However, a more highly-efficient phosphorescent material for a full color display element still needs to be developed.

SUMMARY

An embodiment provides an organometallic complex that efficiently emits light.

Another embodiment provides an organic electroluminescent device using the organometallic complex.

Yet another embodiment provides a display device including the organic electroluminescent device.

According to an embodiment, an organometallic complex represented by Chemical Formula 1 is provided.

Chemical Formula 1

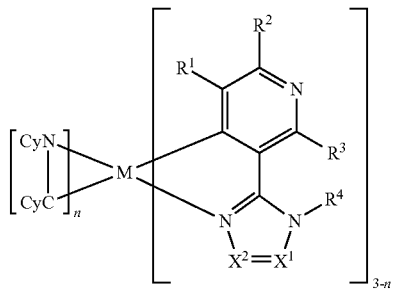

In Chemical Formula 1,

M is Ir, Os, Pt, Pb, Re, Ru, or Pd,

CyN is a substituted or unsubstituted C2 to C60 heterocyclic group wherein nitrogen is bonded to M, or a substituted or unsubstituted C3 to C60 heteroaryl group wherein nitrogen is bonded to M, CyC is a substituted or unsubstituted C4 to C60 carbon cyclic group wherein carbon is bonded to M, a substituted or unsubstituted C3 to C60 heterocyclic group wherein carbon is bonded to M, a substituted or unsubstituted C3 to C60 heterocyclic group wherein nitrogen is bonded to M, a substituted or unsubstituted C3 to C60 aryl group wherein carbon is bonded to M, a substituted or unsubstituted C3 to C60 heteroaryl group wherein carbon is bonded to M, a substituted or unsubstituted C3 to C60 heteroaryl group wherein nitrogen is bonded to M, or a carboxy group wherein oxygen is bonded to M, CyN-CyC is a cyclometalating ligand bonded to M through nitrogen, oxygen, or carbon, $X^1$ and $X^2$ are each independently N or CR', $R^1$ to $R^4$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, wherein $R^3$ and $R^4$ are optionally connected to form a fused ring, and n is an integer ranging from 0 to 2.

The organometallic complex may be represented by Chemical Formula 2.

Chemical Formula 2

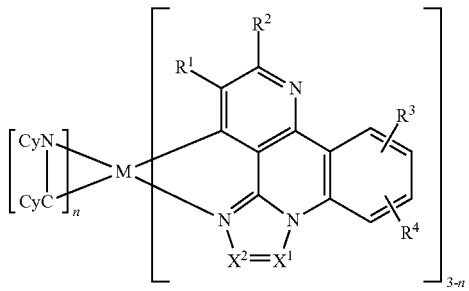

In Chemical Formula 2,

M is Ir, Os, Pt, Pb, Re, Ru, or Pd,

CyN is a substituted or unsubstituted C2 to C60 heterocyclic group wherein nitrogen is bonded to M, or a substituted or unsubstituted C3 to C60 heteroaryl group wherein nitrogen is bonded to M, CyC is a substituted or unsubstituted C4 to C60 carbon cyclic group wherein carbon is bonded to M, a substituted or unsubstituted C3 to C60 heterocyclic group wherein carbon is bonded to M, a substituted or unsubstituted C3 to C60 heterocyclic group wherein nitrogen is bonded to M, a substituted or unsubstituted C3 to C60 aryl group wherein carbon is bonded to M, a substituted or unsubstituted C3 to C60 heteroaryl group wherein carbon is bonded to M, a substituted or unsubstituted C3 to C60 heteroaryl group wherein nitrogen is bonded to M, or a carboxy group wherein oxygen is bonded to M.

CyN-CyC is a cyclometalating ligand bonded to M through nitrogen, oxygen, and carbon, $X^1$ and $X^2$ are each independently N or CR', $R^1$ to $R^4$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, and n is an integer ranging from 0 to 2.

The cyclometalating ligand may be represented by Chemical Formula S-1.

Chemical Formula S-1

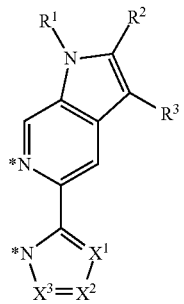

In Chemical Formula S-1, $X^1$ to $X^3$ are each independently N or CR', provided that at least one of $X^1$ to $X^3$ is N, $R^1$ to $R^3$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, wherein at least two of $R^1$ to $R^3$ are optionally connected to form a fused ring, and

* indicates a binding position to M of Chemical Formula 1.

The cyclometalating ligand may be represented by Chemical Formula S-2:

Chemical Formula S-2

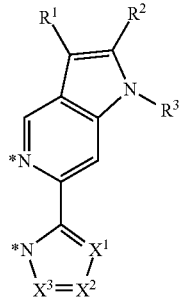

In Chemical Formula S-2,

X$^1$ to X$^3$ are each independently N or CR', provided that at least one of X$^1$ to X$^3$ is N, R$^1$ to R$^3$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF$_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, wherein at least two of R$^1$ to R$^3$ are optionally connected to form a fused ring, and

* indicates a binding position with M of Chemical Formula 1.

The cyclometalating ligand may be represented by the following Chemical Formula S-3.

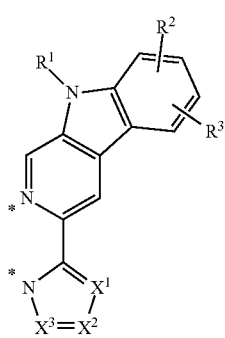

Chemical Formula S-3

In Chemical Formula S-3,

X$^1$ to X$^3$ are independently N or CR', provided that at least one of X$^1$ to X$^3$ is N, R$^1$ to R$^3$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF$_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, and

* indicates a binding position to M of Chemical Formula 1.

The cyclometalating ligand may be represented by Chemical Formula S-4.

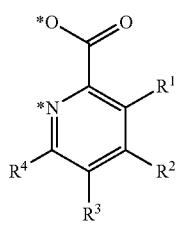

Chemical Formula S-4

In Chemical Formula S-4,

R$^1$ to R$^4$ are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF$_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, or two adjacent substituents of R$^1$ to R$^4$ are fused to form a fused ring, and

* indicates a binding position to M of Chemical Formula 1.

The cyclometalating ligand may be represented by Chemical Formula S-5.

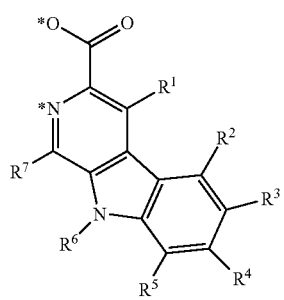

Chemical Formula S-5

In Chemical Formula S-5,

R$^1$ to R$^7$ are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, and \* indicates a binding position with M of the above Chemical Formula 1.

The cyclometalating ligand may be one of the following chemical formulae.

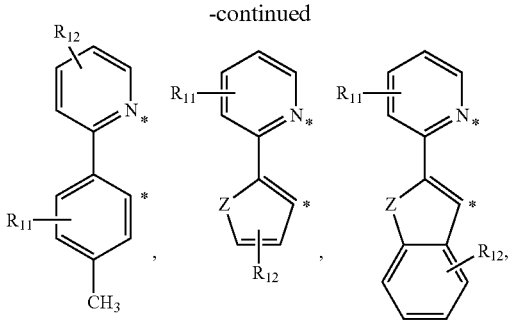

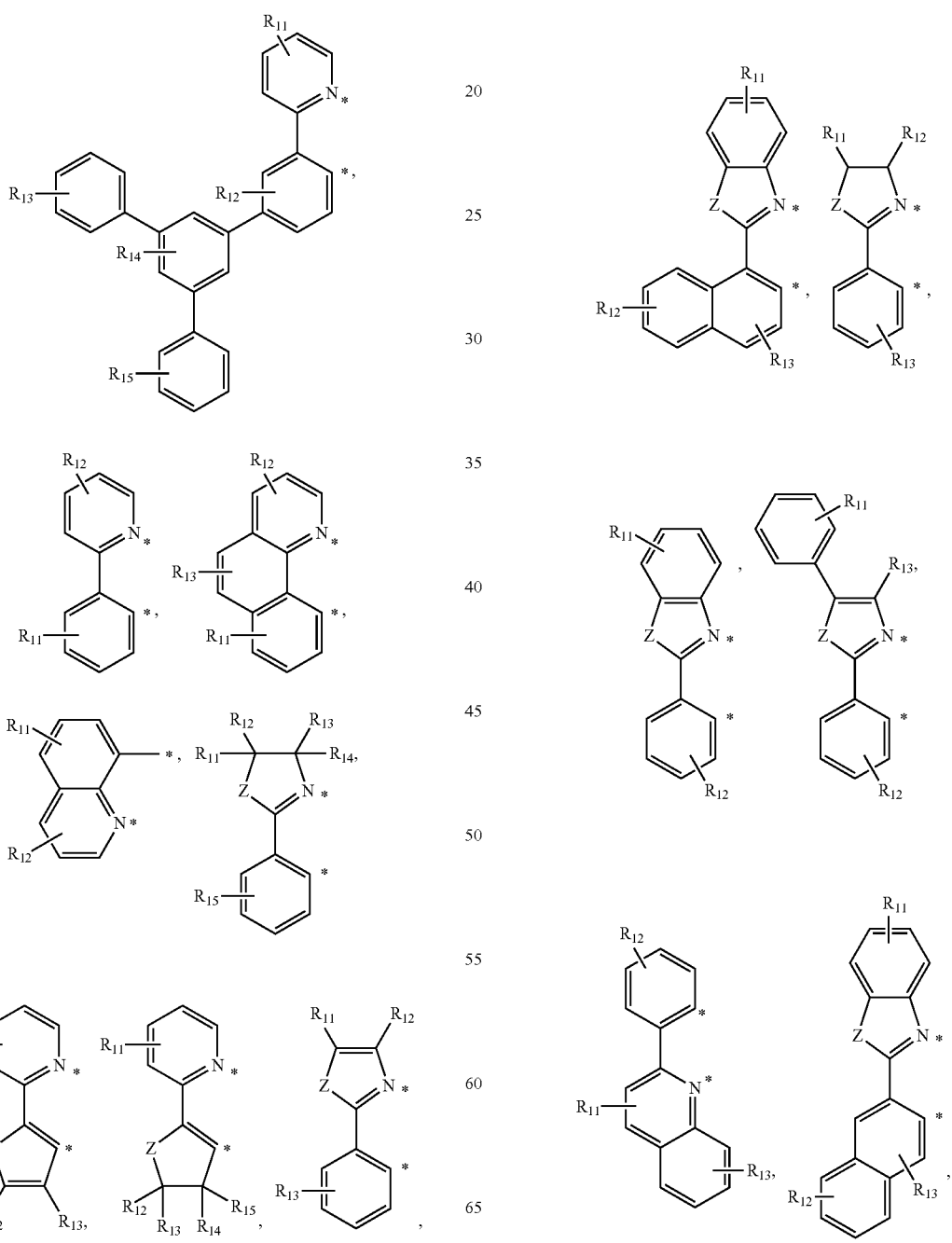

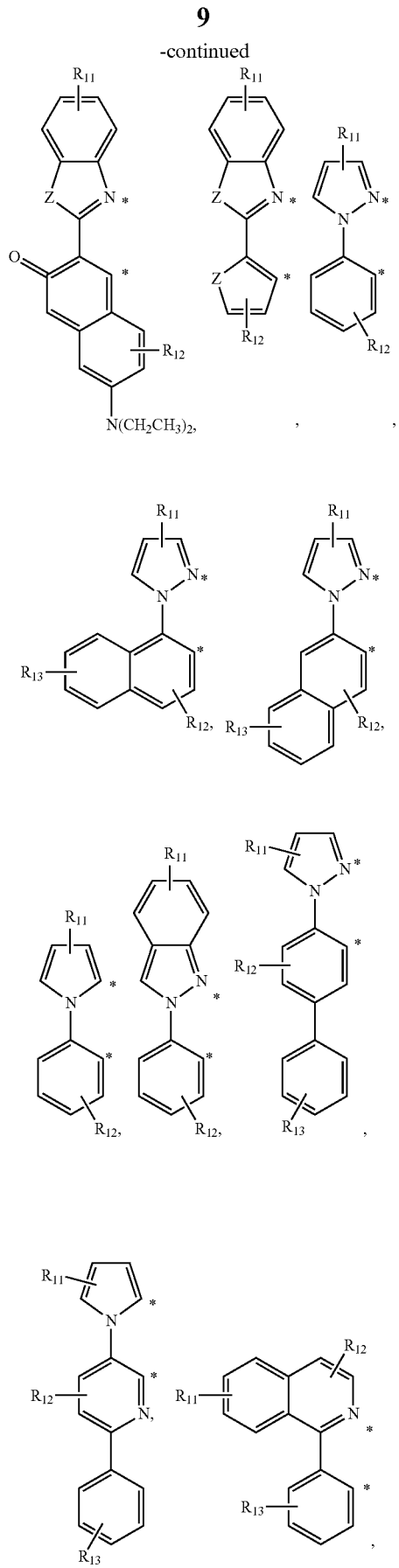
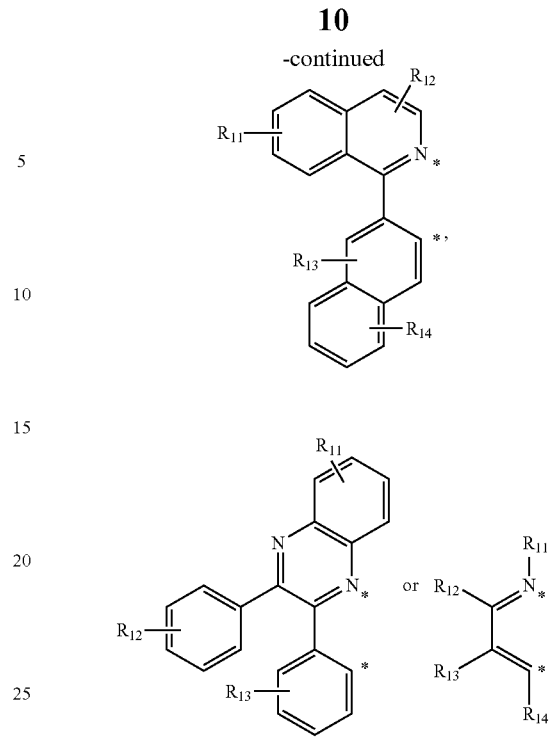
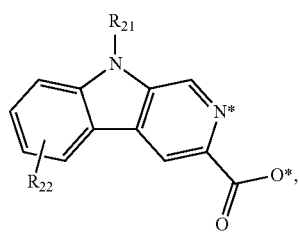

In the chemical formulae, $R^{11}$, $R^{12}$, $R^{13}$, $R^{14}$, and $R^{15}$ are each independently a monosubstituted or multisubstituted functional group, and are each independently hydrogen, a halogen, —OR, —N(R)$_2$, —P(R)$_2$, —P(O)(R)$_2$, —P(O)(OR)$_2$, —P(OR)$_2$, —SR, —Si(R)$_3$, —B(R)$_2$, —B(OR)$_2$, —C(O)R, —C(O)OR, —C(O)N(R), —CN, —NO$_2$, —S(O)R, —S(O)$_2$R, —S(O)$_2$(OR), a C1 to C20 alkyl group, or a C6 to C20 aryl group, wherein R is hydrogen, deuterium, a halogen, a substituted or unsubstituted C1 to C20 alkyl group, a substituted or unsubstituted C1 to C10 alkoxy group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C6 to C40 aryl group, a substituted or unsubstituted C7 to C40 arylalkyl group, a substituted or unsubstituted C7 to C40 alkylaryl group, a substituted or unsubstituted C2 to C40 heteroaryl group, or a substituted or unsubstituted C3 to C40 heteroarylalkyl group, Z is S, O, or NR$^0$ (wherein R$^0$ is hydrogen or a C1 to C20 alkyl group), and

* indicates a binding position with M of Chemical Formula 1.

The cyclometalating ligand may be one of chemical formulae.

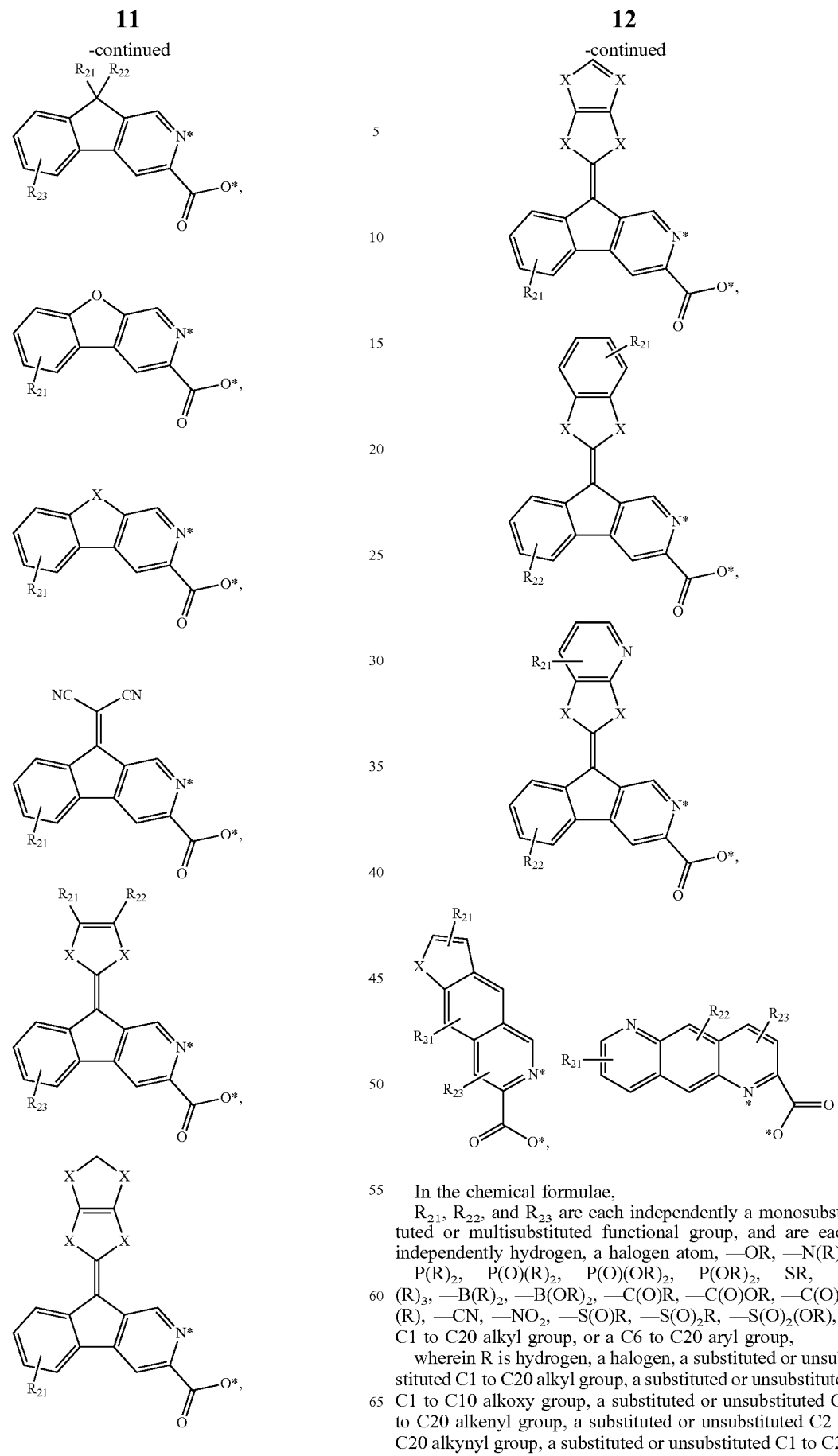

In the chemical formulae,
$R_{21}$, $R_{22}$, and $R_{23}$ are each independently a monosubstituted or multisubstituted functional group, and are each independently hydrogen, a halogen atom, —OR, —N(R)$_2$, —P(R)$_2$, —P(O)(R)$_2$, —P(O)(OR)$_2$, —P(OR)$_2$, —SR, —Si(R)$_3$, —B(R)$_2$, —B(OR)$_2$, —C(O)R, —C(O)OR, —C(O)N(R), —CN, —NO$_2$, —S(O)R, —S(O)$_2$R, —S(O)$_2$(OR), a C1 to C20 alkyl group, or a C6 to C20 aryl group,
wherein R is hydrogen, a halogen, a substituted or unsubstituted C1 to C20 alkyl group, a substituted or unsubstituted C1 to C10 alkoxy group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C6 to C40 aryl group, a substituted or unsubstituted C7 to C40 arylalkyl group, a substituted or unsubstituted C7 to C40 alkylaryl group, a substituted or unsubstituted C2 to C40 heteroaryl group, or a substituted or unsubstituted C3 to C40 heteroarylalkyl group, X is oxygen or sulfur, and

* indicates a binding position to M of Chemical Formula 1.

M may be Ir or Pt.

The organometallic complex represented by the above Chemical Formula 1 may be represented by one of Chemical Formulae A-1 to A-29:

A-1
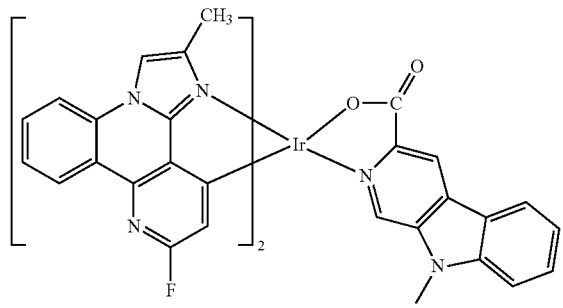

A-2
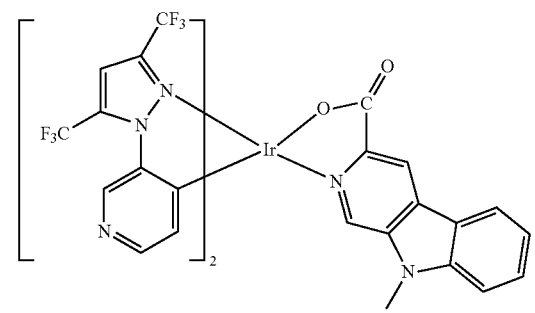

A-3
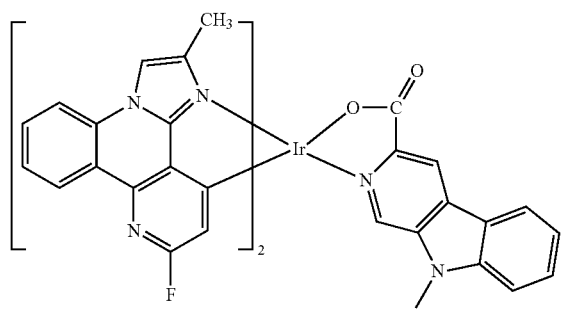

A-4
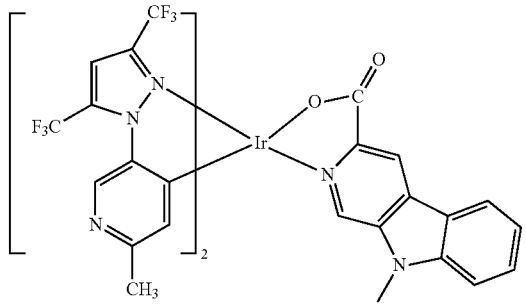

A-5
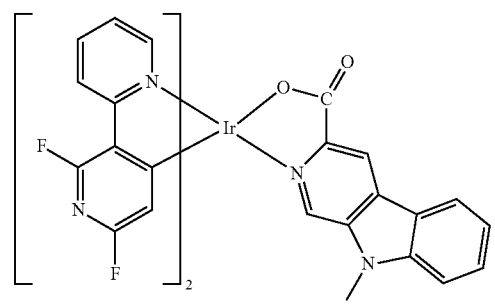

A-6
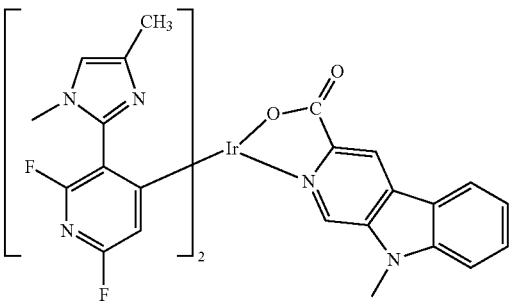

A-7
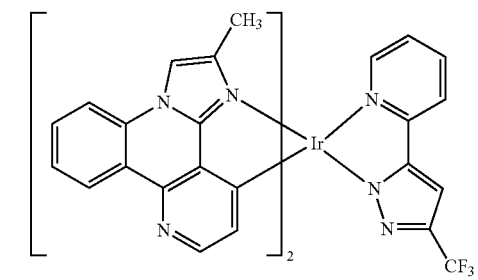

A-8

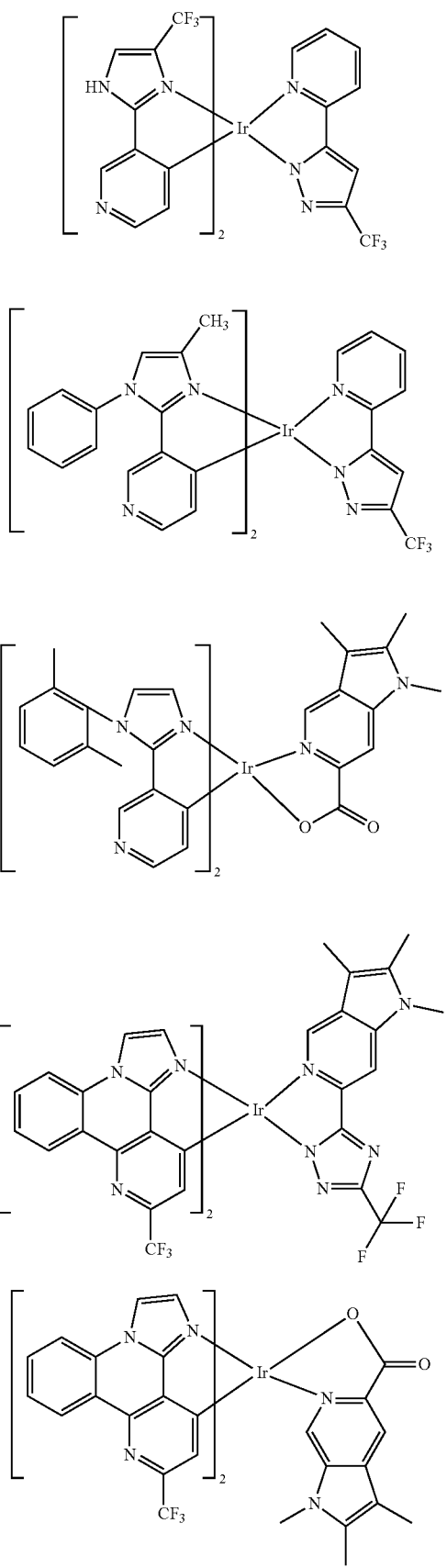
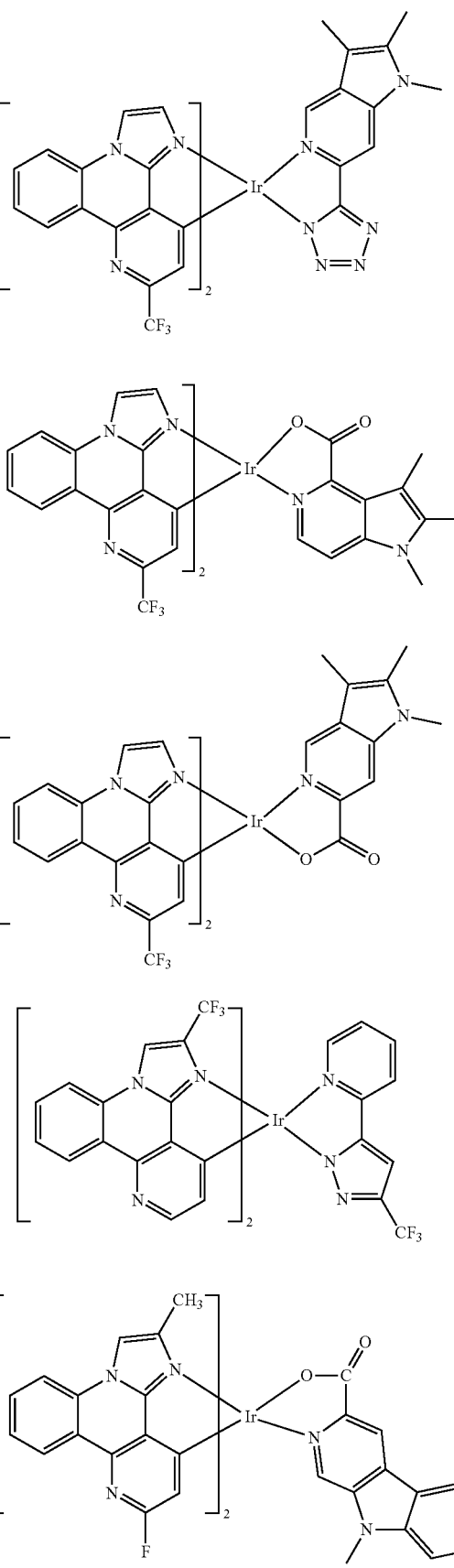

A-19
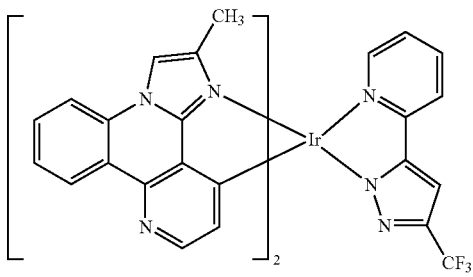
A-20
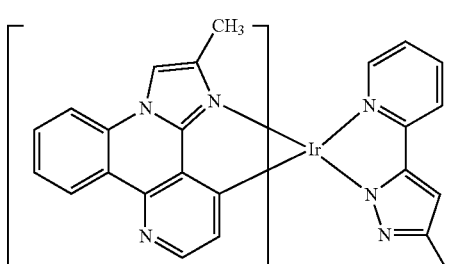
A-21
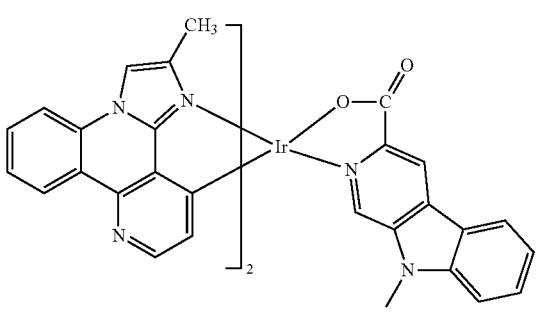
A-22
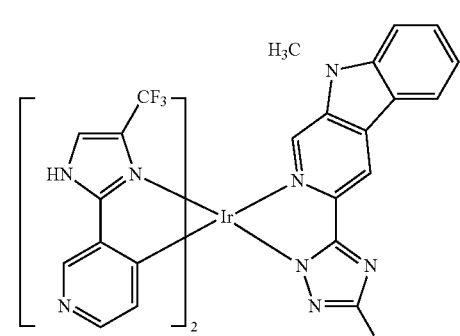
A-23
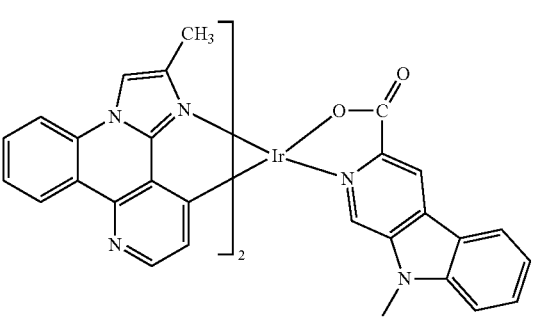
A-24
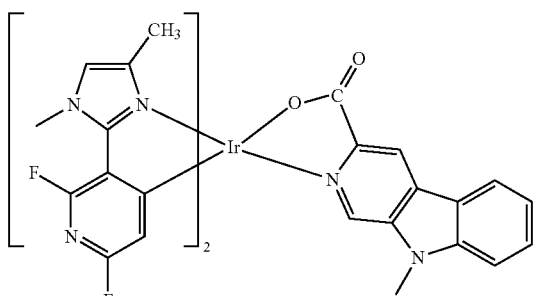
A-25
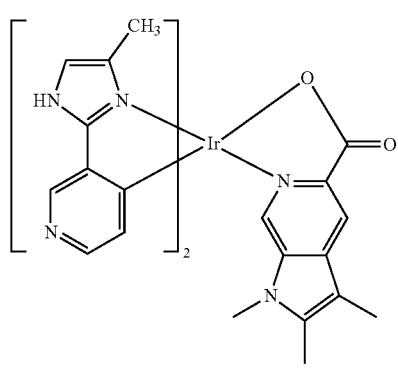
A-26
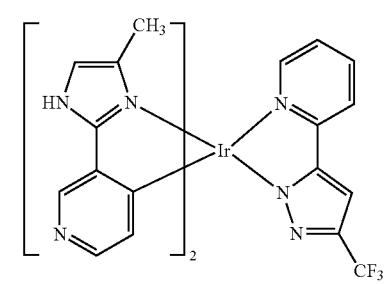
A-27
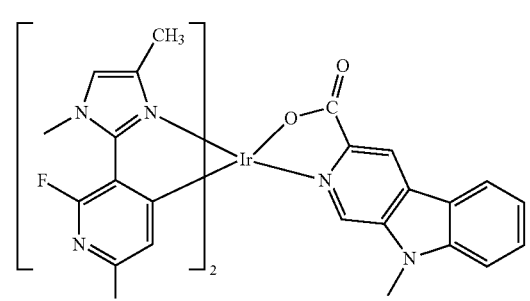
A-28
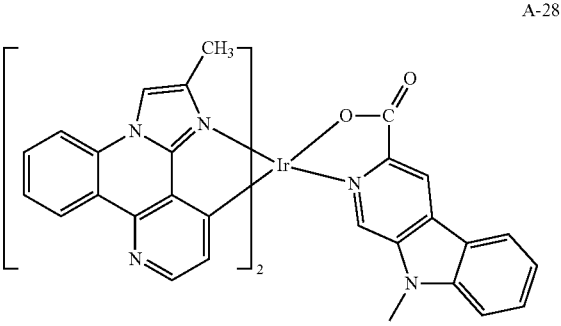

-continued

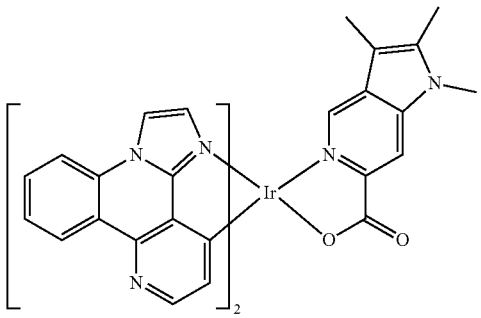

A-29

According to another embodiment, an organic electroluminescent device including a first electrode, a second electrode, and an organic layer disposed between the first and second electrodes, wherein the organic layer includes the organometallic complex according to an embodiment, is provided.

The organic layer may be an emission layer.

The organometallic complex may be included in an amount of about 1 to about 30 parts by weight based on 100 parts by weight of an emission layer-forming material.

According to yet another embodiment, a display device including the organic electroluminescent device is provided.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1A:
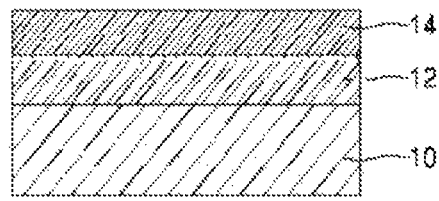
FIGS. 1A to 1F schematically show the lamination structure of an organic electroluminescent device according to an embodiment.

This disclosure will be described more fully hereinafter with reference to the accompanying drawings, in which exemplary embodiments are shown. This disclosure may, however, be embodied in many different forms and is not to be construed as limited to the exemplary embodiments set forth herein; rather, these embodiments are provided so that this disclosure will fully convey the scope of the invention to those skilled in the art. Thus, in some exemplary embodiments, well known technologies are not specifically explained to avoid ambiguous understanding of the present disclosure. Unless otherwise defined, all terms used in the specification (including technical and scientific terms) may be used with meanings commonly understood by a person having ordinary knowledge in the art. Further, unless explicitly defined to the contrary, the terms defined in a generally-used dictionary are not ideally or excessively interpreted. In addition, unless explicitly described to the contrary, the word "comprise" and variations such as "comprises" or "comprising" will be understood to imply the inclusion of stated elements but not the exclusion of any other elements.

Unless specifically described to the contrary, a singular form includes a plural form.

The exemplary embodiments of the present disclosure described in the specification are explained referring to ideal exemplary drawings of schematic diagrams. Therefore, the parts exemplified in the drawings have outline properties and they are not to limit the categories of the invention. The same reference numerals designate the same constituent elements throughout the specification.

As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween. In contrast, when an element is referred to as being "directly on" another element, there are no intervening elements present.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an" and "the" are intended to include the plural forms as well, unless the context clearly indicates otherwise. Unless specified otherwise, the term "or" means "and/or."

Furthermore, relative terms, such as "lower" or "bottom" and "upper" or "top," may be used herein to describe one element's relationship to other elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below. Expressions such as "at least one of," when preceding a list of elements, modify the entire list of elements and do not modify the individual elements of the list.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

As used herein, when a definition is not otherwise provided, the term "substituted" refers to one substituted with at least a functional group selected from deuterium, a halogen, a hydroxyl group, an amino group, a substituted or unsubstituted C1 to C30 amine group, a nitro group, a substituted or unsubstituted C3 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group, or a cyano group, instead of at least one hydrogen of a substituent or a compound.

Two adjacent substituents of the substituted amino group, substituted or unsubstituted C1 to C20 amine group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, C1 to C10 trifluoroalkyl group such as a trifluoromethyl group, and cyano group may be fused to form a ring.

As used herein, when specific definition is not otherwise provided, the term "hetero" refers to one including heteroatoms selected from N, O, S, and P, and including 1 to 3 heteroatoms in one ring and remaining carbon.

As used herein, when specific definition is not otherwise provided, the term "combination thereof" may refer to two or more substituents being bound through a linking group, or two or more substituents condensed to each other.

As used herein, when specific definition is not otherwise provided, the term "alkyl group" refers to an aliphatic hydrocarbon group having the specified number of carbon atoms. The alkyl group may be any saturated alkyl group without a double bond or a triple bond.

The alkyl group may be a C1 to C20 alkyl group. The alkyl group may be a C1 to C10 alkyl group or a C1 to C6 alkyl group. For example, a C1 to C4 alkyl group may have 1 to 4 carbon atoms and may be selected from methyl, ethyl, propyl, iso-propyl, n-butyl, iso-butyl, sec-butyl, and t-butyl.

Examples of the alkyl group may be a methyl group, an ethyl group, a propyl group, an iso-propyl group, a butyl group, an iso-butyl group, a t-butyl group, a pentyl group, a hexyl group, a cyclopropyl group, a cyclobutyl group, a cyclopentyl group, a cyclohexyl group, and the like.

The term "halogen" refers to fluorine, bromine, chlorine, or iodine.

The term "alkoxy" refers to "alkyl-O-", wherein the alkyl is the same as described above and having the specified number of carbon atoms.

The term "cycloalkyl" (or in alternative "carbon cyclic") refers to a saturated hydrocarbon ring group, having only carbon ring atoms and having the specified number of carbon atoms.

The term "cycloalkoxy" refers to "cycloalkyl-O-", wherein the cycloalkyl is the same as described above and having the specified number of carbon atoms.

As used herein, the term "alkenyl" refers to an aliphatic hydrocarbon group, having at least one double bond, and having the specified number of carbon atoms.

As used herein, the term "alkynyl" refers to an aliphatic hydrocarbon, having at least one triple bond, and having the specified number of carbon atoms.

The term "heteroalkyl" refers to an alkyl group having the specified number of carbon atoms, wherein at least one of the carbon atoms is replaced with a heteroatom selected from N, O, S, and P.

The term "aryl group" refers to a substituent including all elements of the cycle having p-orbitals which form conjugation. The "aryl group" may refer to a monocyclic or fused ring polycyclic (i.e., rings sharing adjacent pairs of carbon atoms) substituent.

The term "arylalkyl" refers to a substituted or unsubstituted aryl group covalently linked to an alkyl group that is linked to a compound and having the specified number of carbon atoms, wherein the aryl and the alkyl are the same as described above.

The term "alkylaryl" refers to a substituted or unsubstituted alkyl group covalently linked to an aryl group that is linked to a compound and having the specified number of carbon atoms, wherein the alkyl and the aryl are the same as described above.

The term "aryloxy" refers to "aryl-O-", wherein the aryl is the same as described above and having the specified number of carbon atoms.

The "heteroaryl group" refers to an aryl group including 1 to 3 heteroatoms selected from the group consisting of N, O, S, and P, and remaining carbons. When the heteroaryl group is a fused ring, 1 to 3 heteroatoms may be present in each ring.

The term "heteroarylalkyl" refers to a substituted or unsubstituted heteroaryl group covalently linked to an alkyl group that is linked to a compound and having the specified number of carbon atoms, wherein the heteroaryl and the alkyl are the same as described above.

The term "heteroaryloxy" refers to "heteroaryl-O-", wherein the heteroaryl is the same as described above and having the specified number of carbon atoms.

The term "amino" as used herein refers to a monovalent group of the general formula NRR having the specified number of carbon atoms, wherein each R is independently hydrogen, or an alkyl group.

The term "arylamino" as used herein refers to a monovalent group of the general formula NRR having the specified number of carbon atoms, wherein each R is independently hydrogen, an alkyl group, or an aryl group, and at least one R is an aryl group.

As used herein, when specific definition is not otherwise provided, the term "heterocyclic group" refers to a cyclic functional group including a heteroatom, for example a cycloalkyl group including a heteroatom, and a cycloalkyl group including two or more heteroatoms.

According to an embodiment, an organometallic complex represented by the following Chemical Formula 1 is provided.

Chemical Formula 1

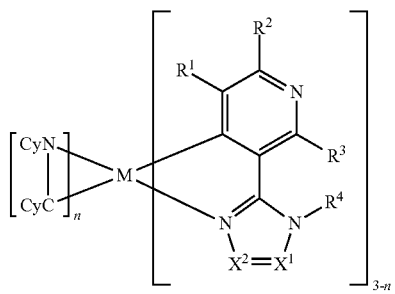

In Chemical Formula 1,
M is Ir, Os, Pt, Pb, Re, Ru, or Pd,
CyN is
a substituted or unsubstituted C2 to C60 heterocyclic group wherein nitrogen is bonded to M, or a substituted or unsubstituted C3 to C60 heteroaryl group wherein nitrogen is bonded to M, CyC is a substituted or unsubstituted C4 to C60 carbon cyclic group wherein carbon is bonded to M, a substituted or unsubstituted C3 to C60 heterocyclic group wherein carbon is bonded to M, a substituted or unsubstituted C3 to C60 heterocyclic group wherein nitrogen is bonded to M, a substituted or unsubstituted C3 to C60 aryl group wherein carbon is bonded to M, a substituted or unsubstituted C3 to C60 heteroaryl group wherein carbon is bonded to M, a substituted or unsubstituted C3 to C60 heteroaryl group wherein nitrogen is bonded to M, or a carboxy group wherein oxygen is bonded to M, CyN-CyC is a cyclometalating ligand bonded to M through nitrogen (N), oxygen (O), or carbon (C), $X^1$ and $X^2$ are each independently N or CR', $R^1$ to $R^4$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, wherein $R^3$ and $R^4$ are optionally connected to form a fused ring, and n is an integer ranging from 0 to 2.

According to an embodiment, an organometallic complex including a novel ancillary ligand and represented by the above Chemical Formula 1 is provided.

The organometallic complex may sufficiently emit red, green, blue ("RGB") light from a triplet metal-to-ligand charge transfer ("MLCT"). The organometallic complex is a thermally stable and highly efficient phosphorescent material emitting light in a region ranging from about 400 to about 700 nanometers ("nm"), and thus may provide RGB light or white light in an organic light-emitting diode ("OLED") and the like.

In the organometallic complex represented by the above Chemical Formula 1, the M is a central metal combining a cyclometalating ligand and/or an ancillary ligand and may include, for example, Ir, Os, Pt, Pb, Re, Ru, or Pd, and specifically Ir or Pt, but is not limited thereto.

The CyN in the above Chemical Formula 1 denotes a heterocyclic group or a heteroaryl group including a nitrogen atom directly forming a coordination bond with the M as a central metal. The heterocyclic group includes a C3 to C60 substituted or unsubstituted heterocyclic group including a heteroatom such as N, O, S, and/or P as a main element forming a cycle, and may be, for example, pyrrolidine, morpholine, thiomorpholine, thiazolidine, and the like, but is not limited thereto.

The heteroaryl group includes a C3 to C60 substituted or unsubstituted heteroaryl group including a heteroatom such as N, O, S, and/or P as a main element forming a cycle, and may be, for example, pyridine, 4-methoxypyridine, quinoline, pyrrole, indole, pyrazine, pyrazole, imidazole, pyrimidine, quinazoline, thiazole, oxazole, triazine, 1,2,4-triazole, and the like, but is not limited thereto.

In CyC of the above Chemical Formula 1, examples of the substituted or unsubstituted C4 to C60 carbon cyclic group wherein carbon is bonded to M may be cyclohexane, cyclopentane, and the like. Examples of the substituted or unsubstituted C3 to C60 heterocyclic group wherein carbon is bonded to M may be tetrahydrofuran, 1,3-dioxane, 1,3-dithiane, 1,3-dithiolane, 1,4-dioxa-8-azaspiro[4,5]decane, 1,4-dioxaspiro[4,5]decan-2-one, and the like. Examples of the substituted or unsubstituted C3 to C60 heterocyclic group wherein carbon is bonded to M may be 1,4-dioxa-8-azaspiro[4,5]decane, 1,4-dioxaspiro[4,5]decan-2-one, and the like. Examples of the substituted or unsubstituted C3 to 60 aryl group wherein carbon is bonded to M may be benzene, 1,3-benzodioxole, biphenyl, terphenyl, naphthalene, anthracene, azulene, and the like. Examples of the substituted or unsubstituted C3 to C60 heteroaryl group wherein carbon is bonded to M may be thiophene, furan, 2(5H)-furanone, pyridine, coumarin, imidazole, 2-phenylpyridine, 2-benzothiazole, 2-benzooxazole, 1-phenylpyrazole, 1-naphthylpyrazole, 5-(4-methoxyphenyl) pyrazole, 2,5-bisphenyl-1,3,4-oxadiazole, 2,3-benzofuran, 2-(4-biphenyl)-6-phenyl benzooxazole, and the like. Examples of the substituted or unsubstituted C3 to C60 heteroaryl group wherein nitrogen is bonded to M may be pyridine, imidazole, 2-phenylpyridine, 2-benzothiazole, 1-phenylpyrazole, 1-naphthylpyrazole, 5-(4-methoxyphenyl)pyrazole, 2,5-bisphenyl-1,3,4-oxadiazole, 2-(4-biphenyl)-6-phenyl benzooxazole, and the like. The carboxy group wherein oxygen is bonded to M has a structure —C(=O)O−. At least one hydrogen of the foregoing groups may be substituted with a C1 to C10 linear or branched alkoxy group, a cyano group, a halogen, and the like.

In Chemical Formula 1, each of the substituents of CyN-CyC may be connected to one another to form a substituted or unsubstituted 4 to 7 atom cyclic group or a substituted or unsubstituted 4 to 7 atom heterocyclic group, and specifically, a fused 4 to 7 atom cyclic or heterocyclic group. Herein, the cyclic group or heterocyclic group may be a C1 to C30 cycloalkyl group, a C1 to C30 heterocycloalkyl group, a C6 to C30 aryl group, or a C4 to C30 heteroaryl group, and each cyclic group or heterocyclic group may be substituted with one or more than one substituent. Herein, "hetero" denotes substitution of a heteroatom such as N, O, P, S, and the like.

In the compound of the above Chemical Formula 1, at least one hydrogen may be substituted with various substituents such as a halogen, —$OR^1$, —$N(R)_2$, —$P(R^1)_2$, —$P(O)(R^1)_2$, —$P(O)(OR^1)_2$, $P(O)(OR^1)_2$, —$P(OR)_2$, —$SR^1$, —$Si(R^1)_3$, —$B(R^1)_2$, —$B(OR^1)_2$, —$C(O)R^1$, —$C(O)OR^1$, —$C(O)N(R^1)$, —CN, —$NO_2$, —$S(O)R^1$, —$S(O)_2R^1$, and —$S(O)_2OR^1$, wherein $R^1$ is selected from hydrogen, a halogen, a substituted or unsubstituted C1 to C20 alkyl group, a substituted or unsubstituted C1 to C10 alkoxy group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C6 to C40 aryl group, a substituted or unsubstituted C7 to C40 arylalkyl group, a substituted or unsubstituted C7 to C40 alkylaryl group, a substituted or unsubstituted C2 to C40 heteroaryl group, and a substituted or unsubstituted C3 to C40 heteroarylalkyl group.

The cyclometalating ligand (CyN-CyC) may be represented by the following Chemical Formula S-1.

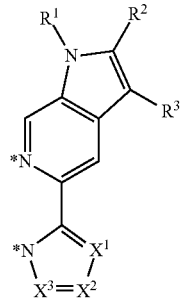

Chemical Formula S-1

In Chemical Formula S-1,
$X^1$ to $X^3$ are each independently N or CR', provided that at least one of $X^1$ to $X^3$ is N,
$R^1$ to $R^3$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group,
wherein at least two of $R^1$ to $R^3$ are optionally connected to form a fused ring, and
* indicates a binding position to M of the above Chemical Formula 1.

The ancillary ligand of the above Chemical Formula S-1 may improve life-span and efficiency of an EL device.

The cyclometalating ligand (CyN-CyC) may be represented by the following Chemical Formula S-2.

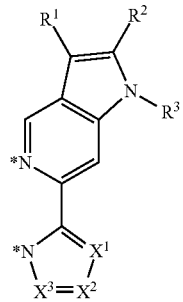

Chemical Formula S-2

In Chemical Formula S-2,
$X^1$ to $X^3$ are each independently N or CR', provided that at least one of $X^1$ to $X^3$ is N,
$R^1$ to $R^3$ and R' are independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group,
wherein at least two of $R^1$ to $R^3$ are optionally connected to form a fused ring, and
* indicates a binding position with M of the above Chemical Formula 1.

The ancillary ligand of the above Chemical Formula S-2 may also improve life-span and efficiency of an EL device.

The cyclometalating ligand (CyN-CyC) may be represented by the following Chemical Formula S-3.

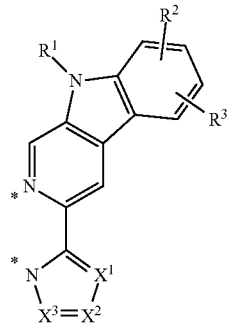

Chemical Formula S-3

In Chemical Formula S-3,
$X^1$ to $X^3$ are each independently N or CR', provided that at least one of $X^1$ to $X^3$ is N,
$R^1$ to $R^3$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, and
* indicates a binding position to M of the above Chemical Formula 1.

The ancillary ligand of the above Chemical Formula S-3 may also improve blue phosphorescence characteristics.

The cyclometalating ligand (CyN-CyC) may be represented by the following Chemical Formula S-4.

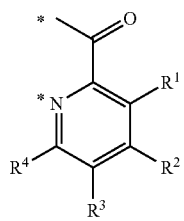

Chemical Formula S-4

In Chemical Formula S-4, $R^1$ to $R^4$ are independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, wherein two adjacent substituents of $R^1$ to $R^4$ are optionally connected to form a fused ring, and

* indicates a binding position to M of the above Chemical Formula 1.

The ancillary ligand of the above Chemical Formula S-4 may also improve blue phosphorescence characteristics.

The cyclometalating ligand (CyN-CyC) may be represented by the following Chemical Formula S-5.

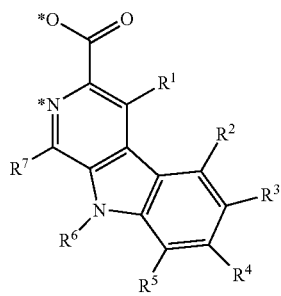

Chemical Formula S-5

In Chemical Formula S-5, $R^1$ to $R^7$ are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, and

* indicates a binding position to M of the above Chemical Formula 1.

The ancillary ligand of the above Chemical Formula S-5 may also improve a color purity of light emitting wavelengths and device efficiency.

The cyclometalating ligand (CyN-CyC) may be one of the following chemical formulae, but is not limited thereto.

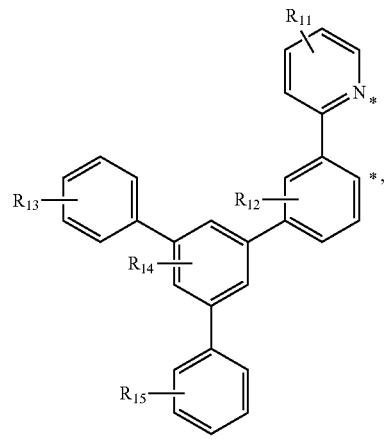

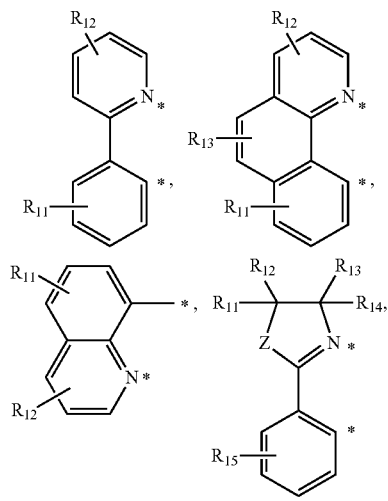

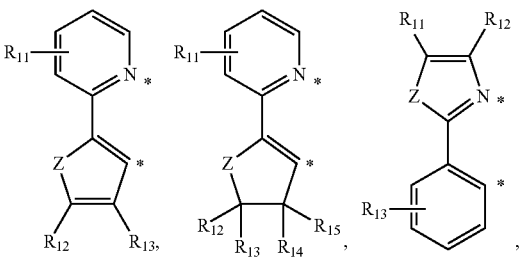

-continued
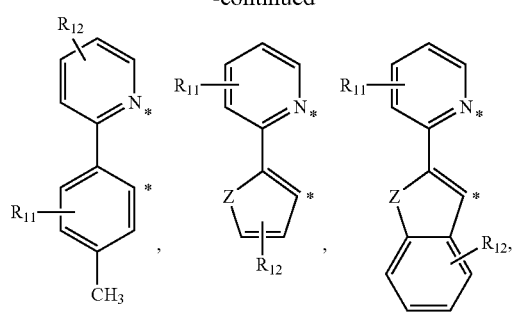
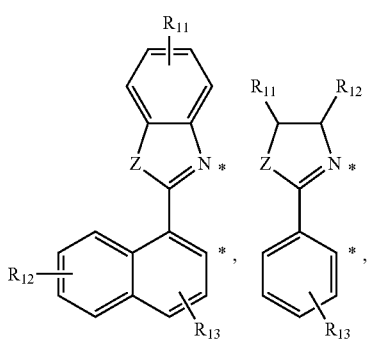
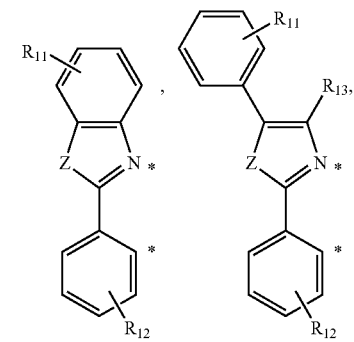
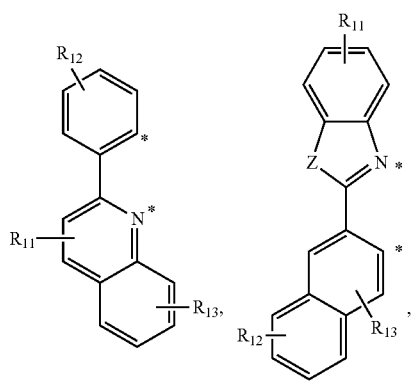
-continued
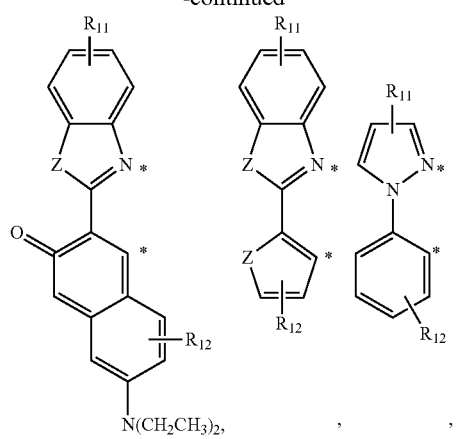
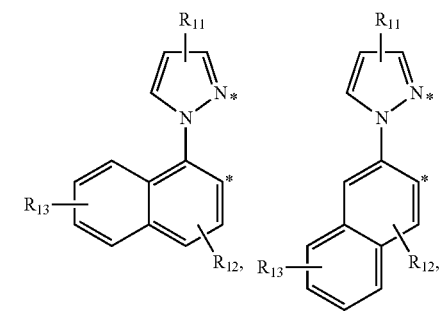
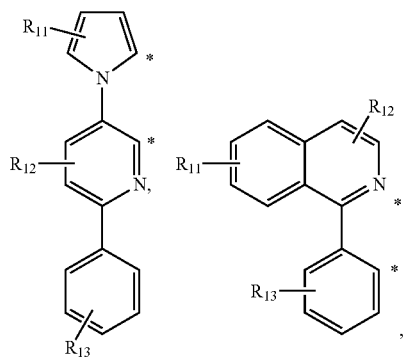

-continued

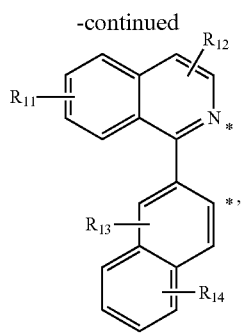

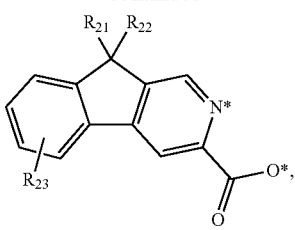

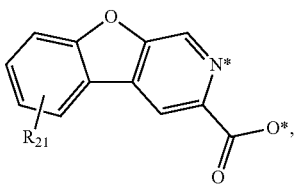

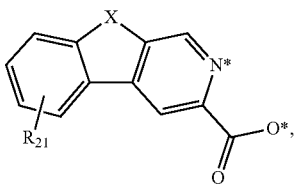

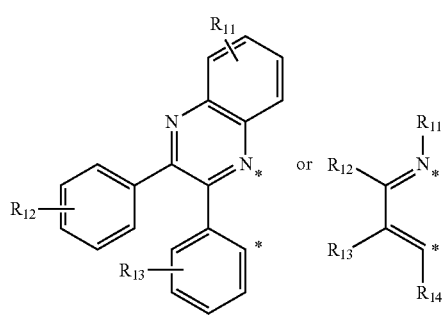

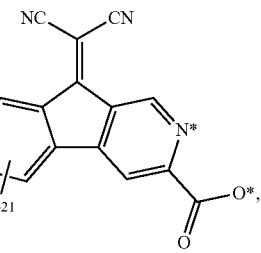

In the chemical formulae, $R^{11}$, $R^{12}$, $R^{13}$, $R^{14}$, and $R^{15}$ are each independently a monosubstituted or multisubstituted functional group, and are each independently hydrogen, a halogen, —OR, —N(R)$_2$, —P(R)$_2$, —P(O)(R)$_2$, —P(O)(OR)$_2$, —P(OR)$_2$, —SR, —Si(R)$_3$, —B(R)$_2$, —B(OR)$_2$, —C(O)R, —C(O)OR, —C(O)N(R), —CN, —NO$_2$, —S(O)R, —S(O)$_2$R, —S(O)$_2$(OR), a C1 to C20 alkyl group, or a C6 to C20 aryl group, wherein R is hydrogen, deuterium, a halogen, a substituted or unsubstituted C1 to C20 alkyl group, a substituted or unsubstituted C1 to C10 alkoxy group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C6 to C40 aryl group, a substituted or unsubstituted C7 to C40 arylalkyl group, a substituted or unsubstituted C7 to C40 alkylaryl group, a substituted or unsubstituted C2 to C40 heteroaryl group, or a substituted or unsubstituted C3 to C40 heteroarylalkyl group, Z is S, O, or NR$^0$ (wherein R$^0$ is hydrogen or a C1 to C20 alkyl group), and \* indicates a binding position to M of the above Chemical Formula 1.

The cyclometalating ligand (CyN-CyC) may be one of the following chemical formulae, but is not limited thereto.

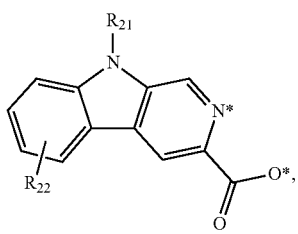

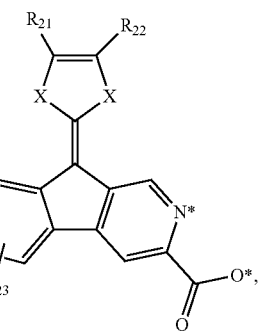

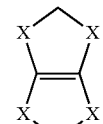

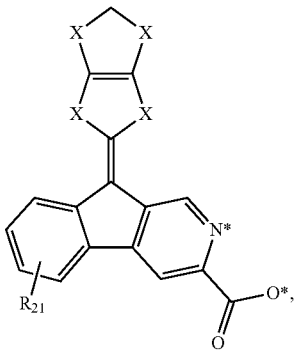

-continued

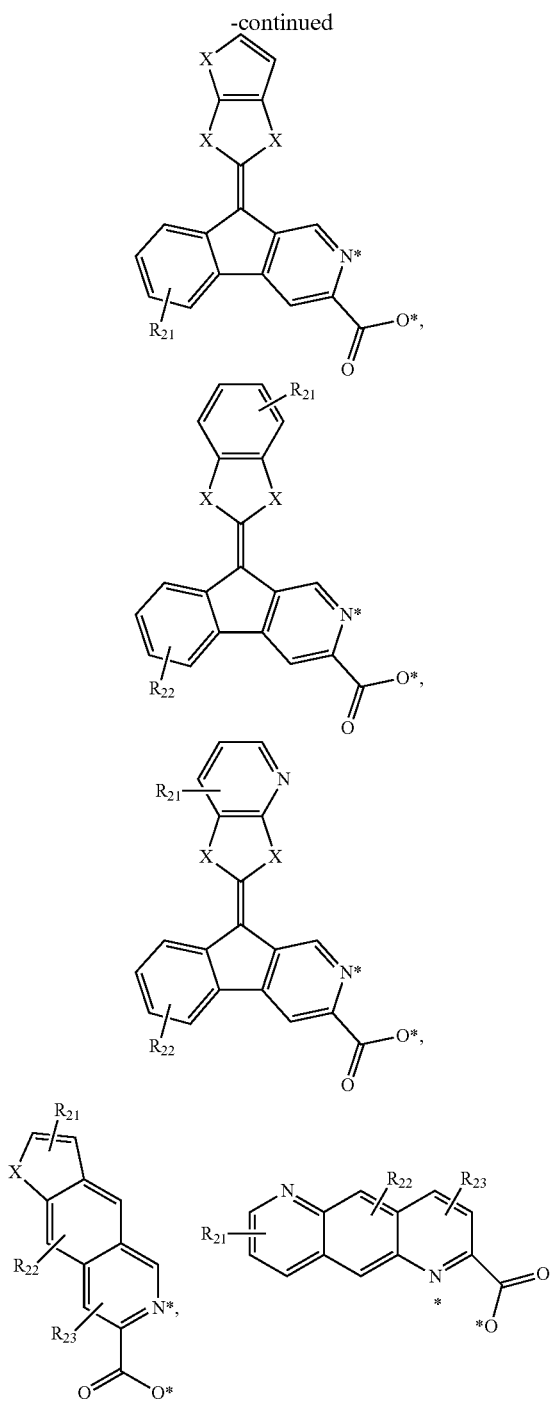

In the chemical formulae, $R_{21}$, $R_{22}$, and $R_{23}$ are each independently a monosubstituted or multisubstituted functional group, and are each independently hydrogen, a halogen atom, —OR, —N(R)$_2$, —P(R)$_2$, —P(O)(R)$_2$, —P(O)(OR)$_2$, —P(OR)$_2$, —SR, —Si(R)$_3$, —B(R)$_2$, —B(OR)$_2$, —C(O)R, —C(O)OR, —C(O)N(R), —CN, —NO$_2$, —S(O)R, —S(O)$_2$R, —S(O)$_2$(OR), a C1 to C20 alkyl group, or a C6 to C20 aryl group, wherein R is hydrogen, a halogen, a substituted or unsubstituted C1 to C20 alkyl group, a substituted or unsubstituted C1 to C10 alkoxy group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C6 to C40 aryl group, a substituted or unsubstituted C7 to C40 arylalkyl group, a substituted or unsubstituted C7 to C40 alkylaryl group, a substituted or unsubstituted C2 to C40 heteroaryl group, or a substituted or unsubstituted C3 to C40 heteroarylalkyl group, X is oxygen or sulfur, and

* indicates a binding position to M of the above Chemical Formula 1.

The organometallic complex may be represented by the following Chemical Formula 2.

Chemical Formula 2

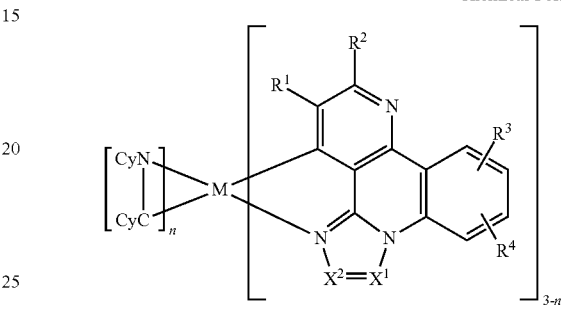

In Chemical Formula 2,

M is Ir, Os, Pt, Pb, Re, Ru, or Pd,

CyN is a substituted or unsubstituted C2 to C60 heterocyclic group wherein nitrogen is bonded to M, or a substituted or unsubstituted C3 to C60 heteroaryl group wherein nitrogen is bonded to M, CyC is a substituted or unsubstituted C4 to C60 carbon cyclic group wherein carbon is bonded to M, a substituted or unsubstituted C3 to C60 heterocyclic group wherein carbon is bonded to M, a substituted or unsubstituted C3 to C60 heterocyclic group wherein nitrogen is bonded to M, a substituted or unsubstituted C3 to C60 aryl group wherein carbon is bonded to M, a substituted or unsubstituted C3 to C60 heteroaryl group wherein carbon bonded to M, a substituted or unsubstituted C3 to C60 heteroaryl group wherein nitrogen is bonded to M, or a carboxy group wherein oxygen is bonded to M, CyN-CyC is a cyclometalating ligand bonded to M through nitrogen (N), oxygen (O), or carbon (C), $X^1$ and $X^2$ are each independently N or CR', $R^1$ to $R^4$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF$_5$, a trialkylsilyl group having a substituted or unsubstituted C1 to C30 alkyl group, a dialkylarylsilyl group having a substituted or unsubstituted C1 to C30 alkyl group and a C6 to C30 aryl group, or a triarylsilyl group having a substituted or unsubstituted C6 to C30 aryl group, and n is an integer ranging from 0 to 2.

The ligand of the above Chemical Formula 2 may improve color purity of blue phosphorescence characteristics.

The organometallic complex represented by the above Chemical Formula 1 may be represented by one of the following Chemical Formulae A-1 to A-29, but is not limited thereto.

A-1

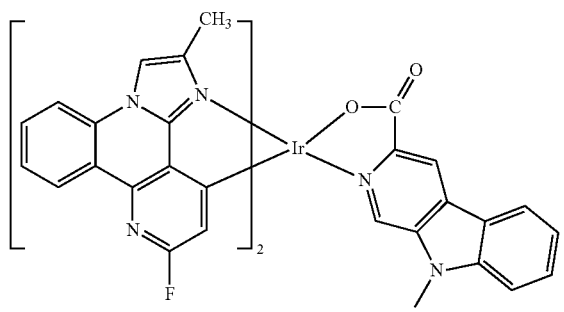

A-2

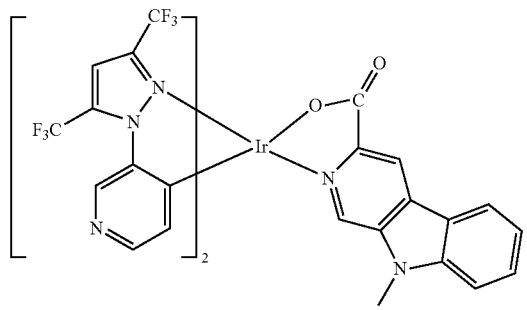

A-3

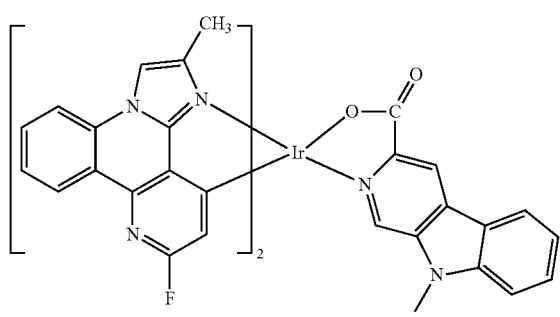

A-4

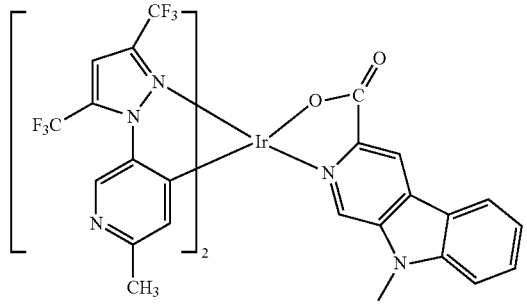

A-5

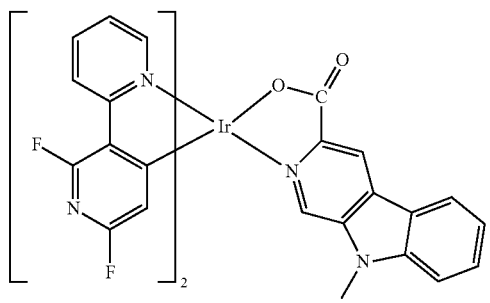

A-6

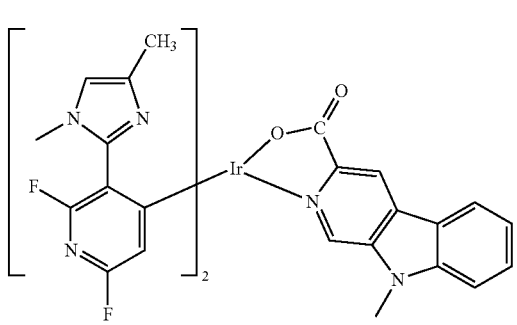

A-7

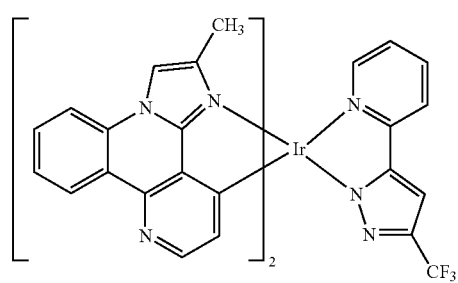

A-8

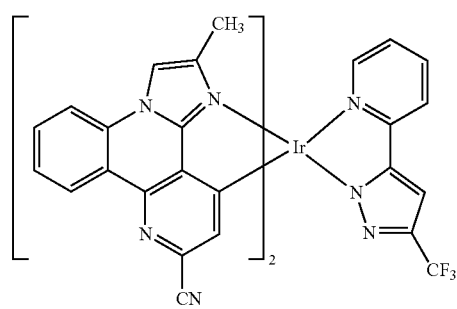

A-9

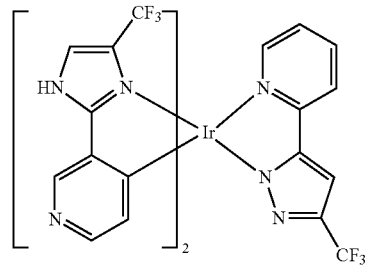

A-10 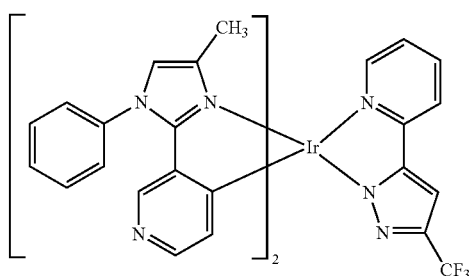
A-11 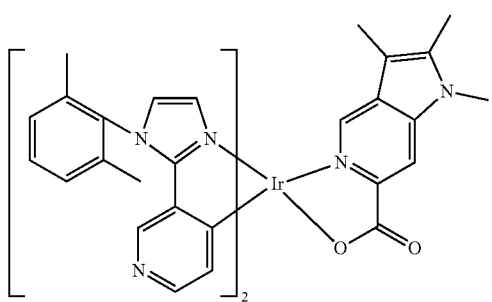
A-12 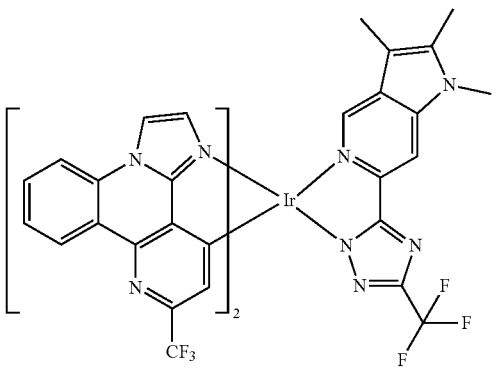
A-13 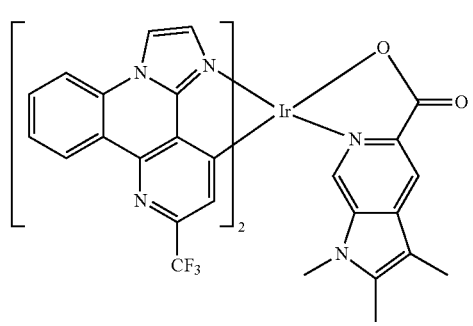
A-14 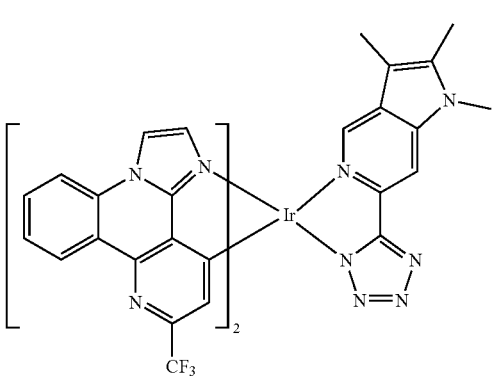
A-15 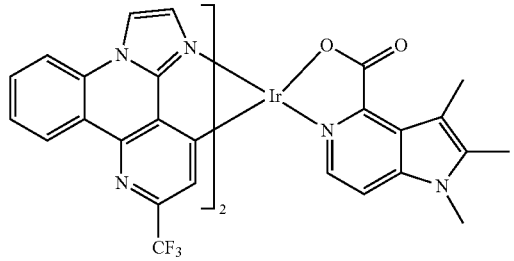
A-16 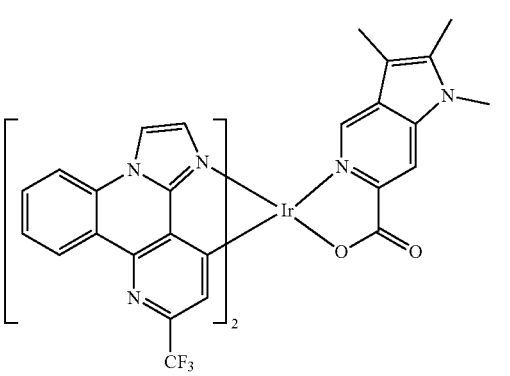
A-17 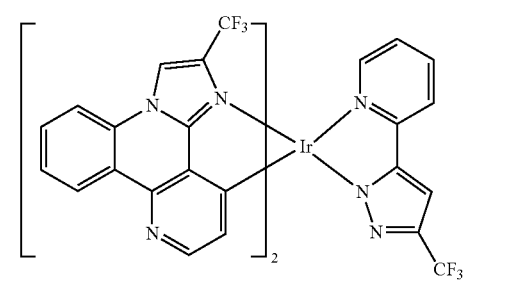
A-18 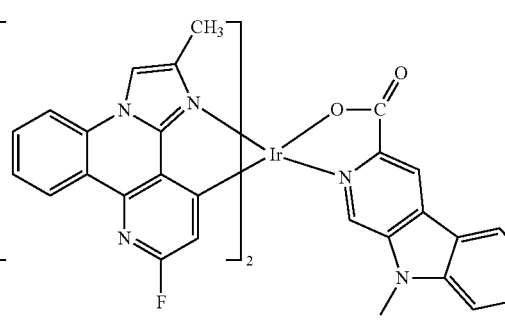
A-19 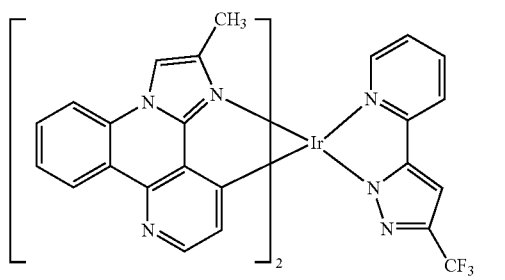

A-20
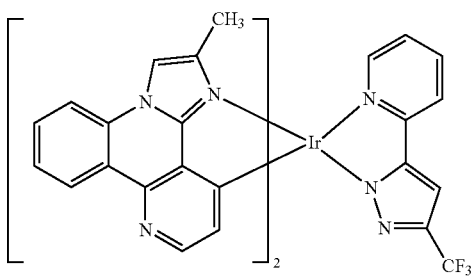
A-21
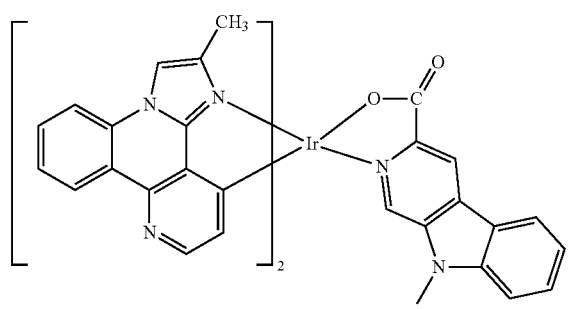
A-22
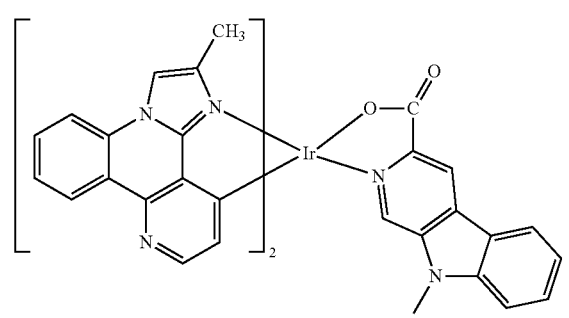
A-23
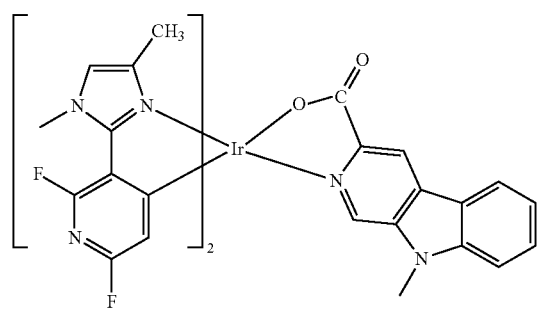
A-25
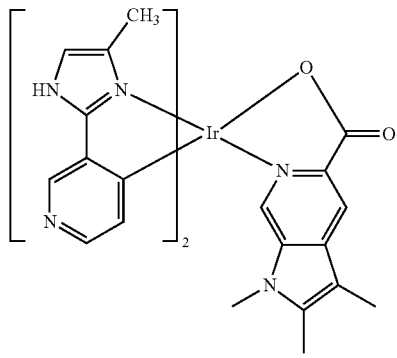
A-26
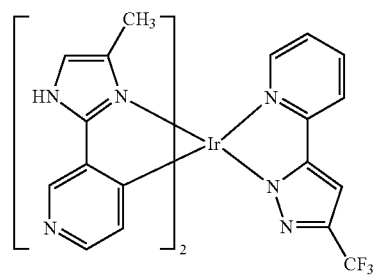
A-27
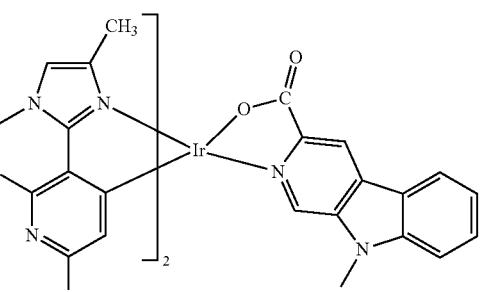
A-28
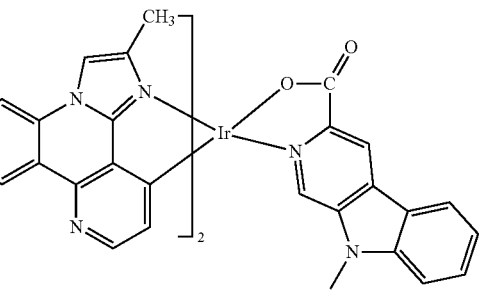
A-29
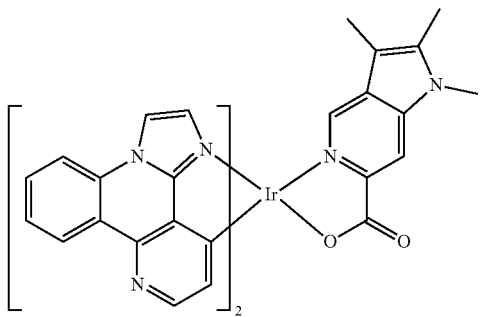

According to an embodiment, an organometallic complex represented by the above Chemical Formula 1 may be synthesized by a method using an [Ir(C^N)$_2$Cl]$_2$ derivative as a starting material providing a cyclometalizing moiety, which is reported by the Watts group (F. O. Garces, R. J. Watts, Inorg. Chem. 1988, 27, 3464).

According to another embodiment, an organic electroluminescent device may be fabricated by using an organometallic complex represented by the above Chemical Formula 1 to form an organic layer, and particularly an emission layer. Herein, the organometallic complex represented by the above Chemical Formula 1 is a phosphorescent dopant material as an emission layer-forming material, and has an excellent light-emitting characteristic in an RGB region.

When the organometallic complex represented by the above Chemical Formula 1 is used as a phosphorescent dopant, an organic layer may further include at least one selected from a polymer host, a mixture host of a polymer and a low molecular host, a low molecular host, and a non-light-emitting polymer matrix. Herein, the polymer host, low molecular host, and non-light-emitting polymer matrix may include a conventional one for forming an emission layer for an organic electroluminescent device. Examples of the polymer host may include PVK (poly (vinylcarbazole)), polyfluorene, and the like. Examples of the low molecular host may include CBP (4,4'-N,N'-dicarbazole-biphenyl), 4,4'-bis[9-(3,6-biphenylcarbazolyl)]-1-1,1'-biphenyl{4,4'-bis[9-(3,6-biphenylcarbazolyl)]-1-1,1-biphenyl}, 9,10-bis[(2',7'-t-butyl)-9',9''-spirobifluorenyl] anthracene, tetrafluorene, and the like. Examples of the non-light-emitting polymer matrix may include polymethylmethacrylate, polystyrene, and the like, but is not limited thereto.

The organometallic complex represented by the above Chemical Formula 1 may be included in an amount of about 1 to about 30 parts by weight, in some embodiments about 1 to about 20 parts by weight, and in other embodiments about 5 to about 20 parts by weight based on 100 parts by weight of the organic layer, for example, an emission layer-forming material. When the organometallic complex is included in an amount of less than about 1 part by weight, a light emitting property of the material is insufficient and efficiency and life-span of the material are deteriorated. When the organometallic complex is included in an amount of greater than about 30 parts by weight, a triplet state is quenched and efficiency is deteriorated. This organometallic complex may be introduced into an emission layer by a method such as vacuum deposition, sputtering, printing, coating, inkjet printing, and the like.

In addition, the organometallic complex represented by the above Chemical Formula 1 may realize various colors depending on combination of a cyclometalating ligand and an ancillary ligand. This organometallic complex may be used with other color light-emitting materials to thus emit white light.

FIGS. 1A to 1F schematically show the lamination structure of an organic electroluminescent device according to an embodiment.

Referring to FIG. 1A, an emission layer 12 including a biphenyl derivative represented by the above Chemical Formula 1 is disposed on a first electrode 10, and a second electrode 14 is disposed on the emission layer 12.

Figure 1B:
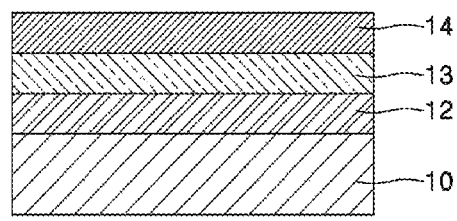

Referring to FIG. 1B, the emission layer 12 including a biphenyl derivative represented by the above Chemical Formula 1 is disposed on the first electrode 10, a hole blocking layer ("HBL") 13 is disposed on the emission layer 12, and the second electrode 14 is disposed on the hole blocking layer ("HBL").

Figure 1C:
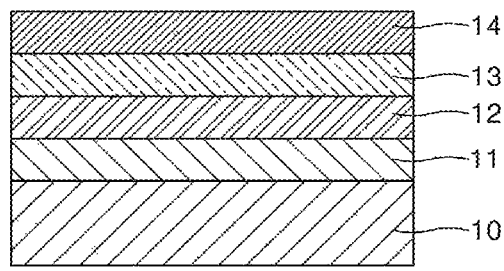

FIG. 1C shows an organic electroluminescent device including a hole injection layer ("HIL") 11 between the first electrode 10 and the emission layer 12. A hole blocking layer ("HBL") 13 is disposed on the emission layer 12, and the second electrode 14 is disposed on the hole blocking layer.

Figure 1D:
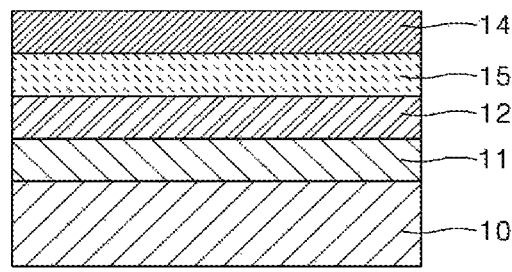

FIG. 1D shows an organic electroluminescent device having the same structure as the one depicted on FIG. 4C, except that an electron transport layer ("ETL") 15 instead of the hole blocking layer (HBL) 13 is formed on the emission layer 12.

Figure 1E:
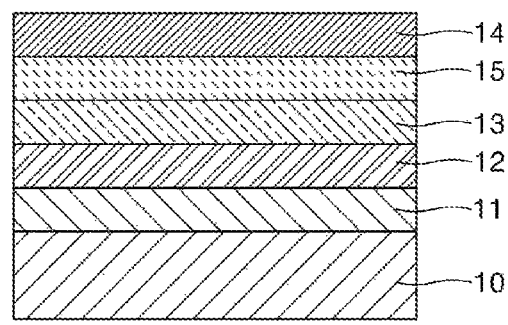

FIG. 1E shows an organic electroluminescent device having the same structure as the one depicted on FIG. 1C, except that the hole blocking layer ("HBL") 13 including a biphenyl derivative represented by Chemical Formula 1 and the electron transport layer ("ETL") 15 are disposed on the emission layer 12. FIG. 1E shows an organic electroluminescent device further including an electron injection layer ("EIL") disposed between the electron transport layer ("ETL") 15 and the second electrode 14.

Figure 1F:
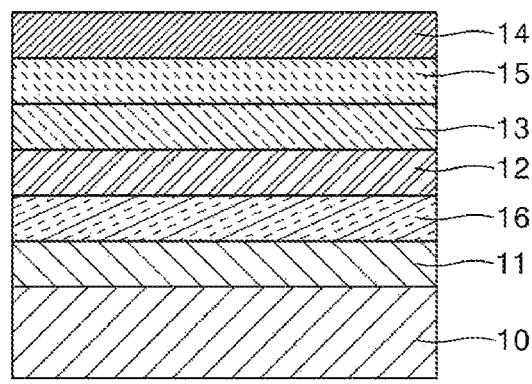
Figure 2:
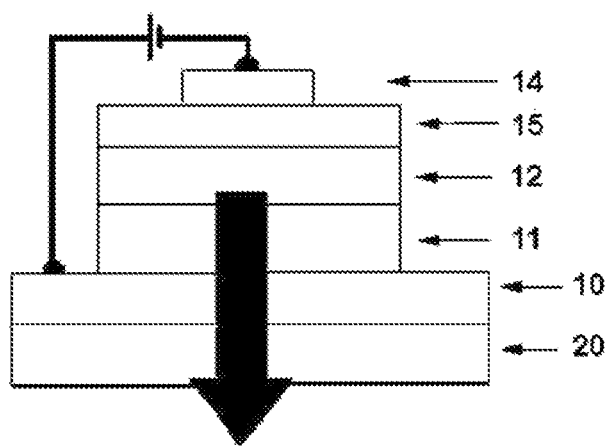
FIG. 2 shows an organic electroluminescent device according to an embodiment.

FIG. 1F shows an organic electroluminescent device having the same structure as the one of FIG. 1E, further including a hole transport layer ("HTL") 16 disposed between the hole injection layer ("HIL") 11 and the emission layer 12.

Herein, the hole transport layer ("HTL") 16 is designed to suppress impurities transmitted from the hole injection layer ("HIL") 11 into the emission layer 12.

The organic electroluminescent device may be fabricated in any suitable conventional method known to one of ordinary skill in the art, but is not limited thereto.

Herein, the organic layer may be about 30 to about 100 nm thick, in some embodiments about 50 to 100 nm thick, and in other embodiments about 50 to 80 nm thick. When the organic layer is less than about 30 nm thick, efficiency and life-span of the organic layer may be deteriorated, and when the organic layer is greater than 100 nm thick, the driving voltage of the organic material may be increased.

On the other hand, the organic layer may be a layer including an organic compound and disposed between a first and second electrodes in an organic electroluminescent device, for example, an electron transport layer ("ETL"), a hole transport layer ("HTL"), and any other layer, except the emission layer.

On the other hand, a buffer layer may be formed between any adjacent layers in the organic electroluminescent device. The buffer layer may be formed of a conventional material such as copper phthalocyanine, polythiophene, polyaniline, polyacetylene, polypyrrole, polyphenylenevinylene, or a derivative thereof, but is not limited thereto.

The hole transport layer ("HTL") may be formed of a conventional material, for example polytriphenylamine, but is not limited thereto.

The electron transport layer ("ETL") may be formed of a conventional material, for example polyoxadiazole, but is not limited thereto.

The hole blocking layer ("HBL") may be formed of a conventional material, for example, LiF, BaF$_2$, MgF$_2$, or the like, but is not limited thereto.

According to an embodiment, the organic electroluminescent device may be fabricated using a common light emitting material without a particular device or method.

The organometallic complex represented by Chemical Formula 1 according to an embodiment may emit light in a wavelength region ranging from about 400 to about 700 nm, in some embodiments from about 500 to about 700 nm, and in other embodiments from about 500 to about 600 nm. When the organometallic complex is used to fabricate a light emitting diode, the light emitting diode may, for example, be used in a light source lamp for a full color display, a backlight, an outdoor bulletin board, optical communication, interior decoration, and the like.

The organometallic complex according to an embodiment has excellent light emitting characteristics, and may form a dopant having excellent phosphorescent characteristics. Specifically, the dopant may be used as a phosphorescent material emitting light in various chromophore regions depending on a strength of an electronic effect displayed by a substituent at the heteroaromatic core of the cyclometalating or ancillary ligand.

In addition, the organometallic complex according to an embodiment has excellent thermal stability. The thermal stability of the organometallic complex may excellently endure firing and the like during the fabrication of a device.

According to another embodiment, a display device including the organic optoelectronic device is provided.

Hereinafter, the embodiments are illustrated in more detail with reference to examples. These examples, however, should not in any sense be interpreted as limiting the scope of the present disclosure.

Synthesis of Organometallic Complex

EXAMPLE 1

Synthesis of Compound A-1

Synthesis of iridium chloro-bridge dimer composite: 1.17 g (5 mmol) of 2-methylbenzo[h]imidazo[2,1-f][1,6]naphthyridine and 0.353 g (1 mmol) of $IrCl_3 \cdot 3H_2O$ are reacted in an ethoxy ethanol including a small amount of water for 3 days to synthesize 0.5 g (yield: 36%) of an iridium chloro-bridge dimer which is used for A-1 synthesis.

Synthesis of A-1 compound: 0.245 g (1.08 mmol) of 9-methyl-9H-pyrido[3,4-b]indole-3-carboxylic acid and 0.11 g of sodium carbonate anhydride are added to 0.5 g (0.36 mmol) of the iridium chloro-bridge dimer in 50 ml of ethoxy ethanol and agitated for 2 days. After the reaction is terminated, products are separated and rinsed with methoxy ethanol and water followed by vacuum drying.

Yield: 0.32 g (50%).

The structure of the compound is identified to have a structure of the above Chemical Formula A-1 through $^1H$ NMR and mass analysis. The complex has a decomposition temperature of greater than or equal to 370° C. which is confirmed by thermogravimetric analysis. The complex is dissolved in 2-methyltetrahydrofuran to prepare a solution. The solution emits light at 461 nm from light emitting wavelength ("PL") that corresponds to a CIE color coordinate of 0.16 and 0.26.

EXAMPLES 2 to 16

Synthesis of Compound Represented by Chemical Formulae A-2 to A-16

The compounds represented by the above Chemical Formulae A-2 to A-16 are synthesized according to a similar method to Example 1.

Reaction scheme of dimer composites of Examples 1 to 16 and resultant compounds are as follows.

Reaction Scheme of Iridium Chloro-Bridge Dimer Composite

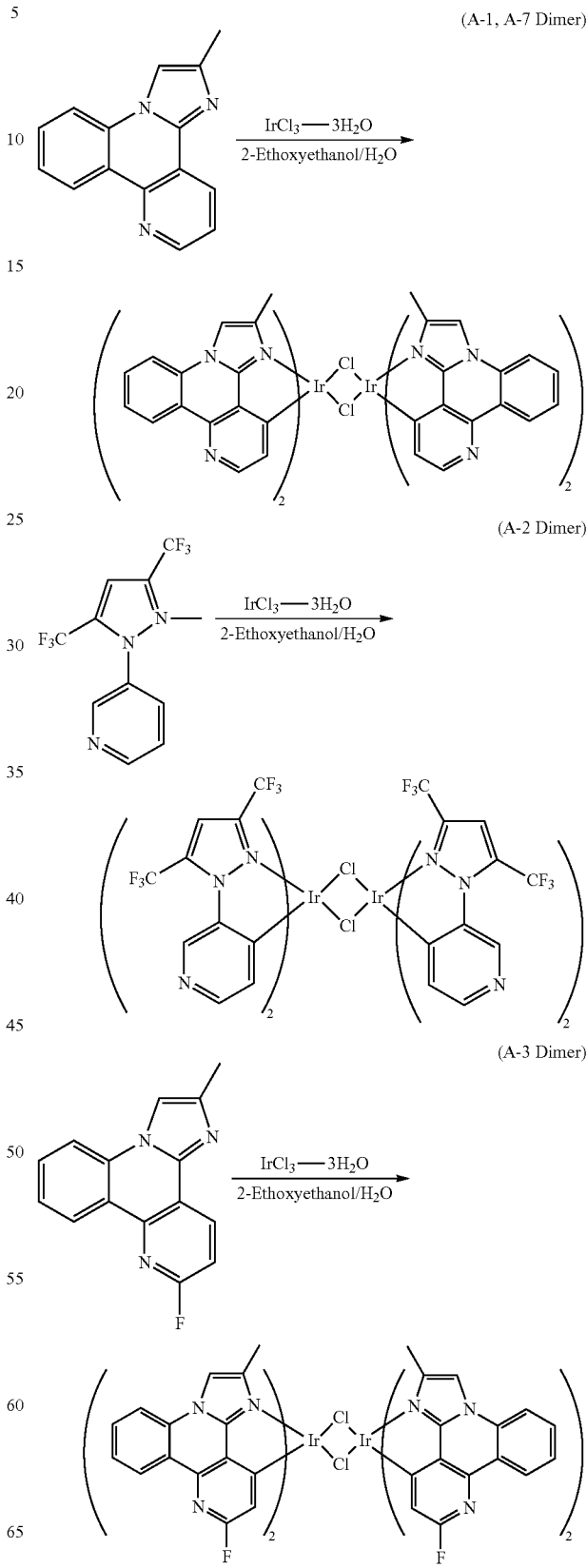

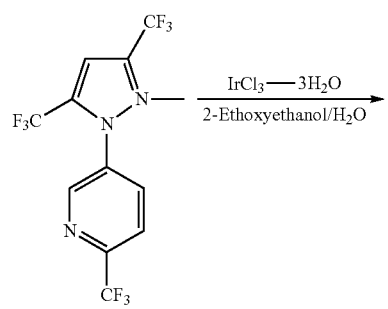
(A-4 Dimer)
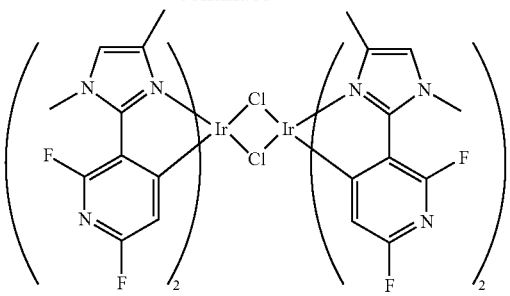
(A-8 Dimer)
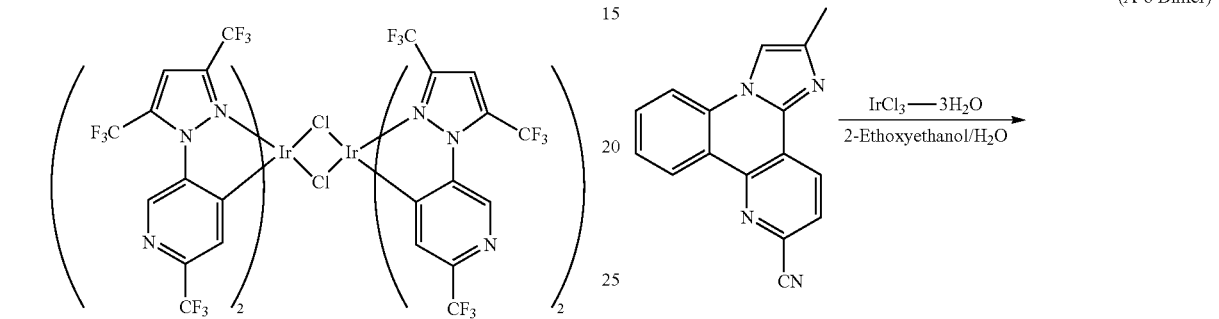
(A-5 Dimer)
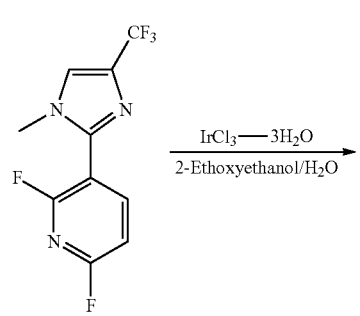
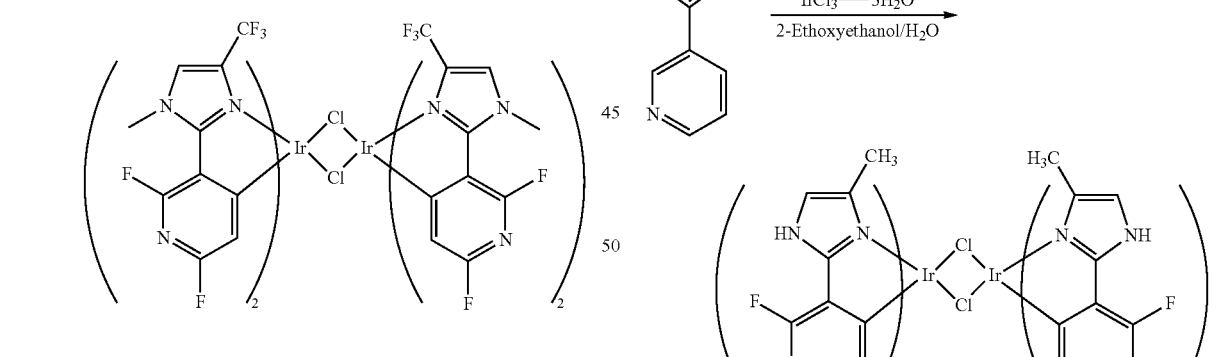
(A-6 Dimer)
(A-9 Dimer)
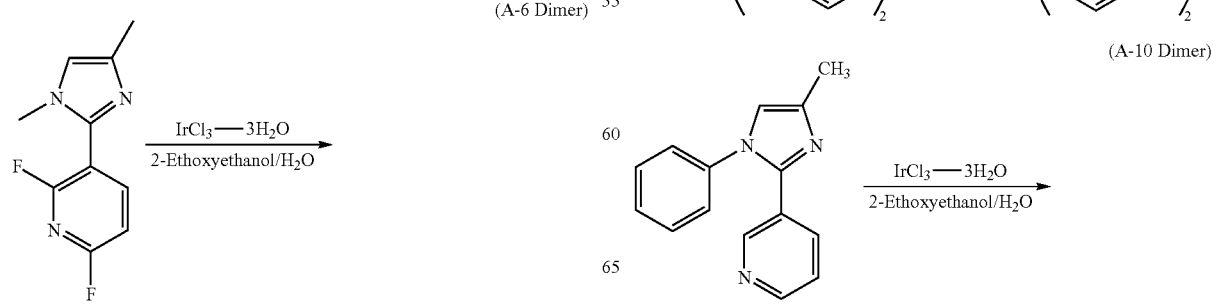
(A-10 Dimer)

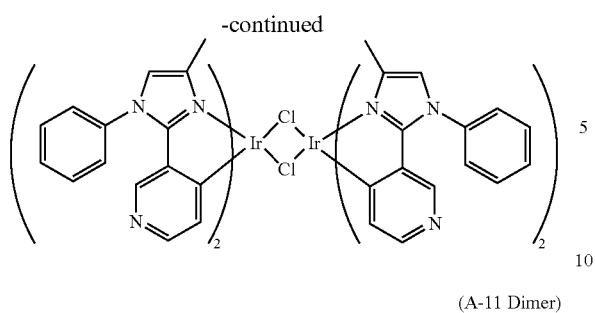
(A-11 Dimer)
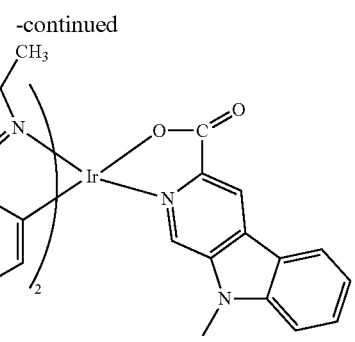
Molecular Weight: 649.70
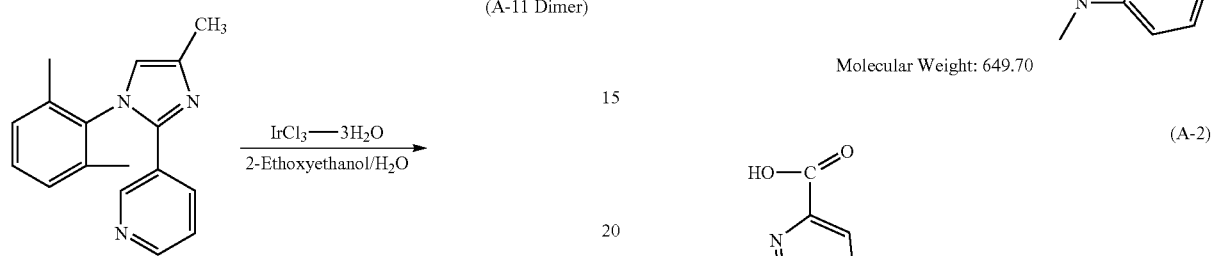
(A-12~16 Dimer)
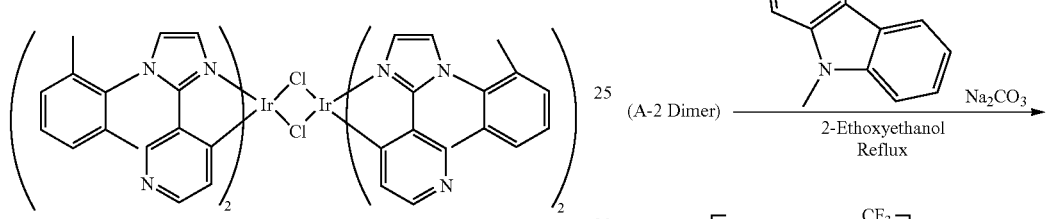
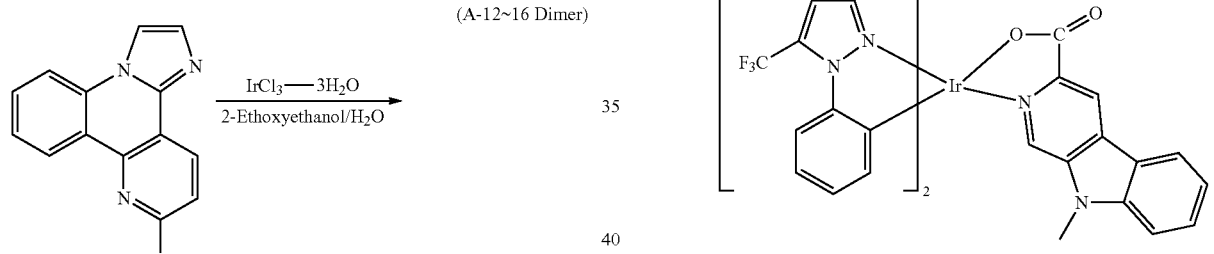
Reaction Scheme of Organometallic Complex Compound
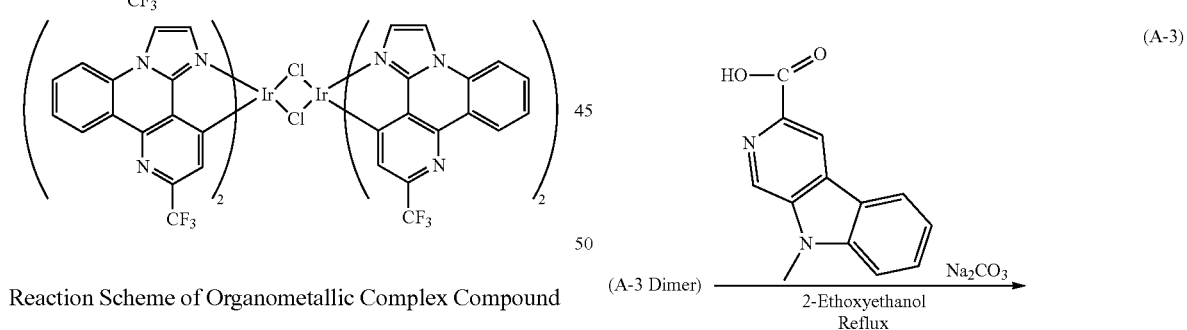
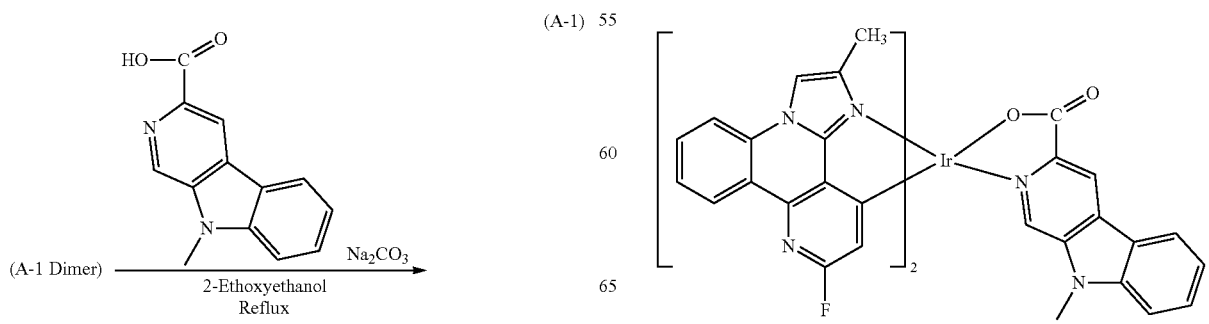

49
-continued
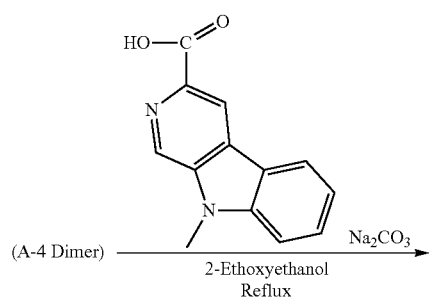
(A-4 Dimer) → Na₂CO₃ / 2-Ethoxyethanol Reflux
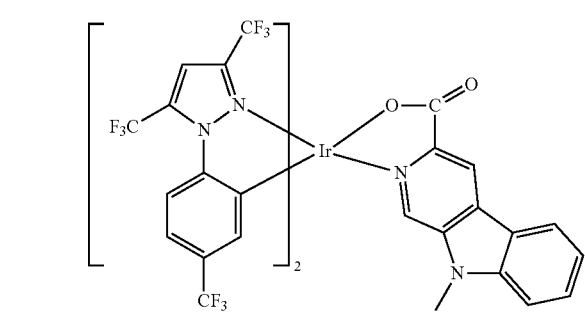
(A-5)
(A-5 Dimer) → Na₂CO₃ / 2-Ethoxyethanol Reflux
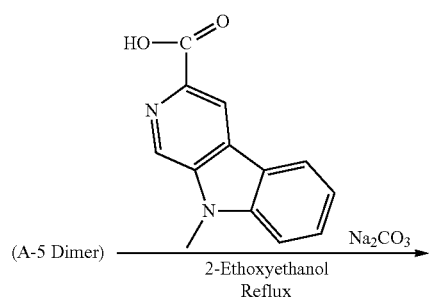
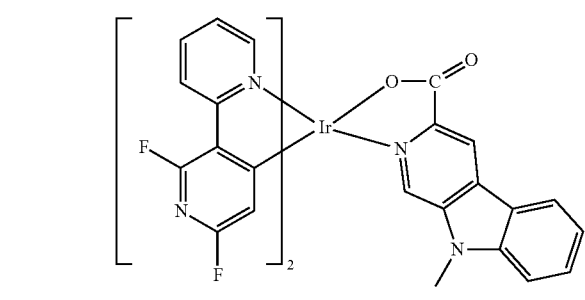
(A-6)
(A-6 Dimer) → Na₂CO₃ / 2-Ethoxyethanol Reflux
50
-continued
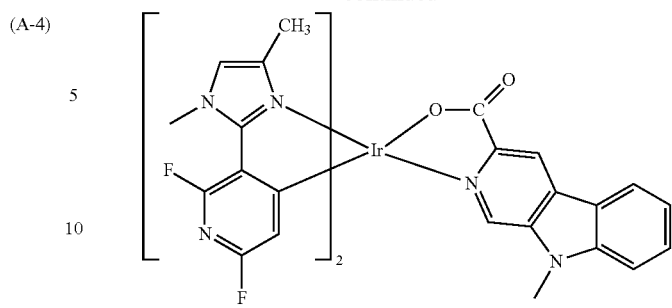
(A-4)
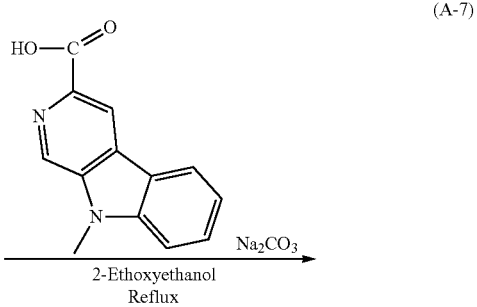
(A-7)
(A-1 Dimer) → Na₂CO₃ / 2-Ethoxyethanol Reflux
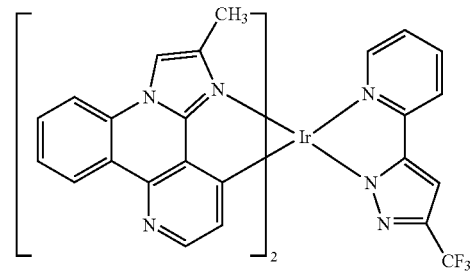
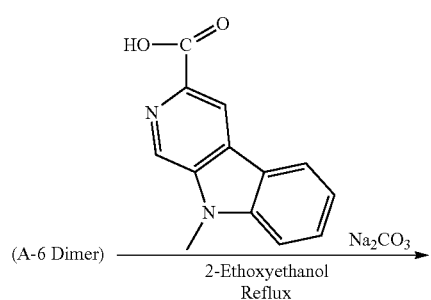
(A-8)
(A-6 Dimer) → Na₂CO₃ / 2-Ethoxyethanol Reflux
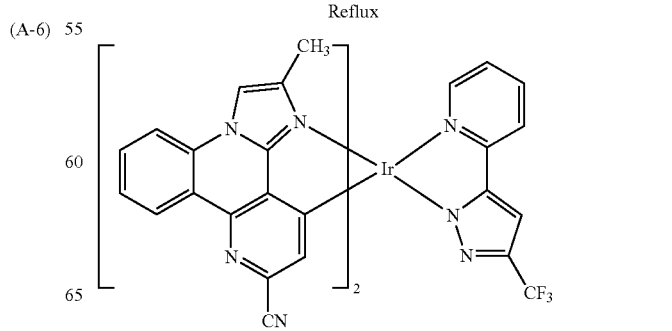

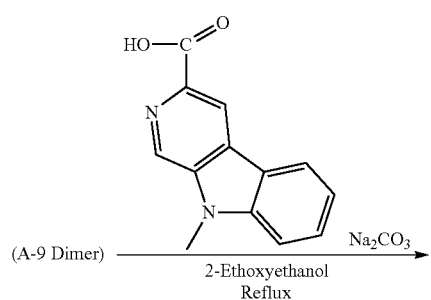
(A-9)
(A-10)
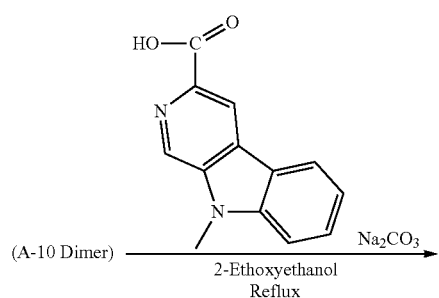
(A-11)
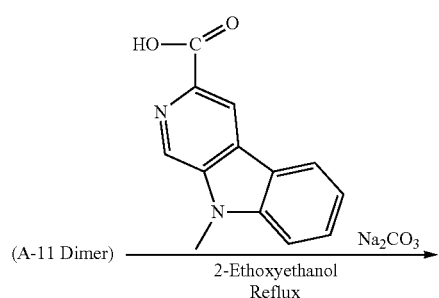
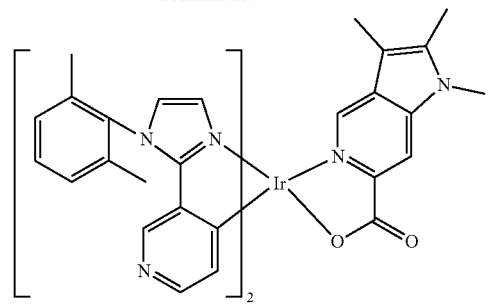
(A-12)
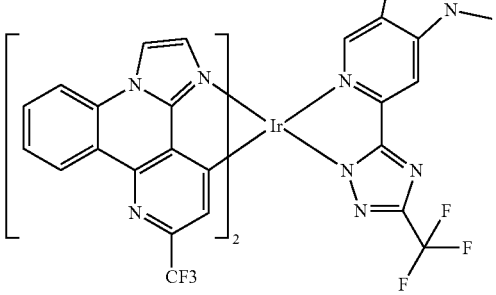
(A-13)
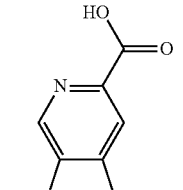
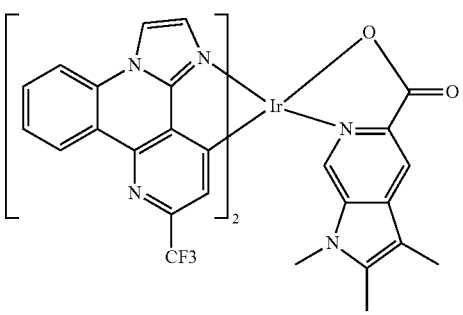

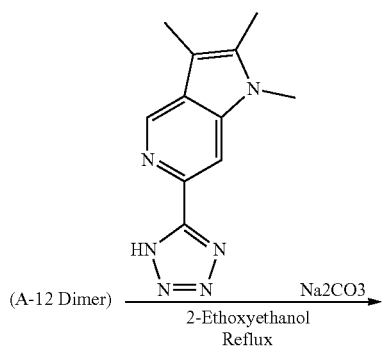

(A-14)

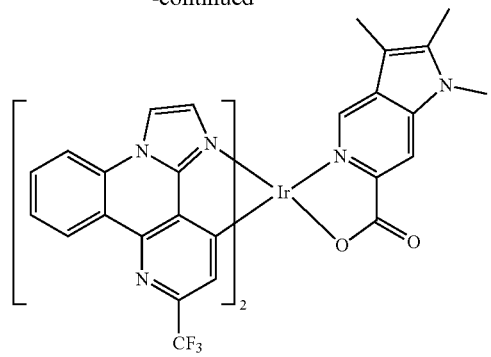

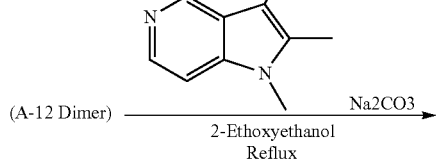

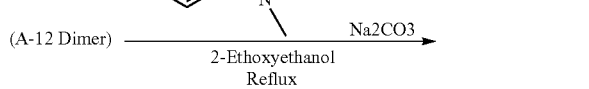

(A-15)

(A-16)

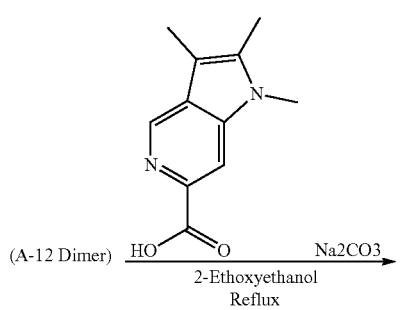

PL analysis results of the complex dissolved in 2-methyltetrahydrofuran are shown in Table 1. Herein, the HOMO value is measured by cyclic voltammetry, and the LUMO value is measured by UV-visible spectroscopy.

TABLE 1

| Code | HOMO (eV) | LUMO (eV) | λemi (PL, nm) |
|---|---|---|---|
| A-1 | 5.3 | 1.7 | 461 |
| A-2 | 5.6 | 1.9 | 492 |
| A-3 | 5.5 | 1.8 | 457 |
| A-4 | 6.0 | 2.3 | 487 |
| A-5 | 6.0 | 2.0 | 472 |
| A-6 | 5.5 | 1.8 | 456 |
| A-7 | 5.5 | 1.5 | 467 |
| A-8 | 5.9 | 2.0 | 472 |
| A-9 | 5.4 | 1.5 | 467 |
| A-10 | 5.5 | 1.5 | 467 |
| A-11 | 4.6 | 0.7 | 464 |
| A-12 | 5.5 | 1.6 | 469 |
| A-13 | 5.6 | 1.5 | 454 |
| A-14 | 5.7 | 1.6 | 461 |
| A-15 | 5.6 | 1.5 | 473 |
| A-16 | 5.6 | 1.5 | 454 |

Fabrication of Organic Electroluminescent Device

PREPARATION EXAMPLE 1

Fabrication of Organic Electroluminescent Device

A transparent electrode substrate coated with ITO (indium-tin oxide) is cleaned, and the ITO is patterned with a photosensitive resin and an etchant to form an ITO pattern. Then, the ITO-patterned transparent electrode substrate is cleaned again. The ITO glass substrate is sonicated in isopropyl alcohol ("IPA"), cleaned, and rinsed with deionized water. The rinsed ITO glass substrate is UV-ozone treated before it is used to fabricate an ITO coated glass substrate device.

On the other hand, a hole transport layer ("HTL"), an emission layer ("EML"), and an electron transport layer ("ETL") are thermally deposited under a thermal vacuum condition of $10^{-7}$ torr. Then, a LiF electrode and an aluminum cathode are formed under a vacuum condition. As for each layer of a phosphorescence device, the electron-transporting material is 1,3,5-tri[(3-pyridyl)-phen-3-yl]benzene ("TmPyPB"), the hole-transporting material is 1,1-bis{4-[N,N'-di(p-tolyl)amino]phenyl}cyclohexane ("TAPC"), and a host material for an emission layer is 9-(4-tert-butylphenyl)-3,6-bis(triphenylsilyl)-9H-carbazole ("CzSi"). The emission layer is a phosphorescent emission layer formed by doping the compound represented by Chemical Formula A-1 at a concentration of 6%. The compound has a specific structure as follows.

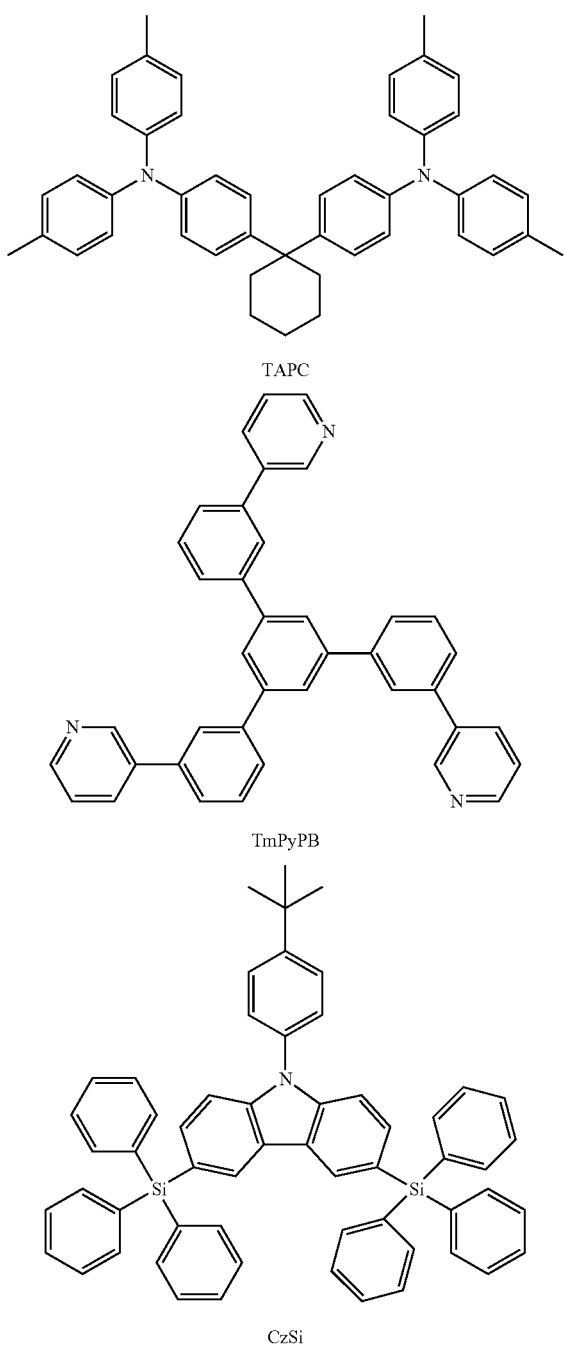

TAPC

TmPyPB

CzSi

Device Characteristic Evaluation

The device according to Preparation Example 1 is evaluated regarding characteristics. The evaluation is performed in the following method.

The devices are measured regarding density-voltage ("J-V") current and luminance-voltage ("L-V") characteristic using a Keithley 2635A meter and a Minolta CS-100A luminance meter, respectively. In addition, the EL (electroluminescence) spectrum and CIE color coordinates of the devices are measured using a Minolta CS-1000A meter.

The EL devices have the following characteristics (measured at 1,000 nit).

TABLE 2

| | EL λmax (nm) | CIE (x, y) | Efficiency @1000 nit (cd/A) | Driving voltage (V) |
|---|---|---|---|---|
| Preparation Example 1 | 463 | 0.16, 0.26 | 9.5 | 6.3 |

Referring to Table 2, an electroluminescent device using a compound according to an embodiment has high luminance and high efficiency, and may be operated at a low voltage.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not to limit the present disclosure in any way.

What is claimed is:

1. An organometallic complex represented by Chemical Formula 1:

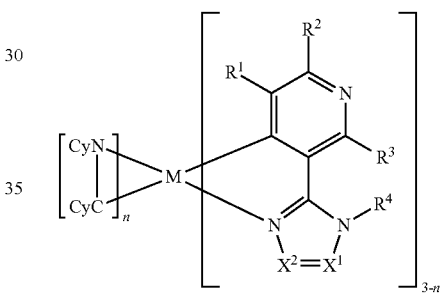

Chemical Formula 1 wherein, in Chemical Formula 1,
M is Ir, Os, Pt, Pb, Re, Ru, or Pd,
CyN is
a substituted C2 to C60 heterocyclic group wherein nitrogen is bonded to M, or
a substituted C3 to C60 heteroaryl group wherein nitrogen is bonded to M,
wherein the substituents of CyN are connected to one another to form a substituted or unsubstituted 4 to 7 atom fused cyclic group or a substituted or unsubstituted 4 to 7 atom fused heterocyclic group,
CyC is
a substituted or unsubstituted C3 to C60 heterocyclic group wherein carbon is bonded to M,
a substituted or unsubstituted C3 to C60 heterocyclic group wherein nitrogen is bonded to M,
a substituted or unsubstituted C3 to C60 heteroaryl group wherein carbon is bonded to M,
a substituted or unsubstituted C3 to C60 heteroaryl group wherein nitrogen is bonded to M, or
a carboxy group wherein oxygen is bonded to M, provided that when CyC is a carboxy group wherein oxygen is bonded to M, the substituents of CyN are connected to one another to form a substituted or unsubstituted fused C1 to C30 cycloalkyl group or a substituted or unsubstituted 4 to 6 atom fused heterocyclic group, CyN-CyC is a cyclometalating ligand bonded to M through nitrogen, oxygen, or carbon, X¹ and X² are each independently N or CR', R¹ to R⁴ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF₅, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group, wherein R³ and R⁴ are optionally connected to form a fused ring, and n is 1 or 2.

2. The organometallic complex of claim 1, wherein the organometallic complex is represented by Chemical Formula 2:

Chemical Formula 2

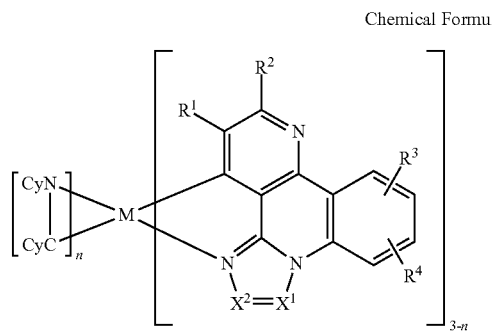

wherein, in Chemical Formula 2,

M is Ir, Os, Pt, Pb, Re, Ru, or Pd,

CyN is a substituted C2 to C60 heterocyclic group wherein nitrogen is bonded to M, or a substituted C3 to C60 heteroaryl group wherein nitrogen is bonded to M, wherein the substituents of CyN are connected to one another to form a substituted or unsubstituted 4 to 7 atom fused cyclic group or a substituted or unsubstituted 4 to 7 atom fused heterocyclic ring, CyC is a substituted or unsubstituted C3 to C60 heterocyclic group wherein carbon is bonded to M, a substituted or unsubstituted C3 to C60 heterocyclic group wherein nitrogen is bonded to M, a substituted or unsubstituted C3 to C60 heteroaryl group wherein carbon is bonded to M, a substituted or unsubstituted C3 to C60 heteroaryl group wherein nitrogen is bonded to M, CyN-CyC is a cyclometalating ligand bonded to M through nitrogen, oxygen, or carbon, X¹ and X² are each independently N or CR', and R¹ to R⁴ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF₅, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group, and n is 1 or 2.

3. The organometallic complex of claim 1, wherein the cyclometalating ligand is represented by Chemical Formula S-1:

Chemical Formula S-1

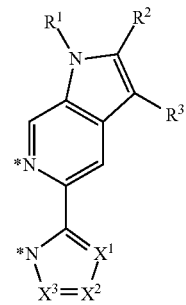

wherein, in Chemical Formula S-1,

X¹ to X³ are each independently N or CR', provided that at least one of X¹ to X³ is N, R¹ to R³ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF₅, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group, wherein at least two of R¹ to R³ are optionally connected to form a fused ring, and

* indicates a binding position to M of Chemical Formula 1.

4. The organometallic complex of claim 1, wherein the cyclometalating ligand is represented by Chemical Formula S-2:

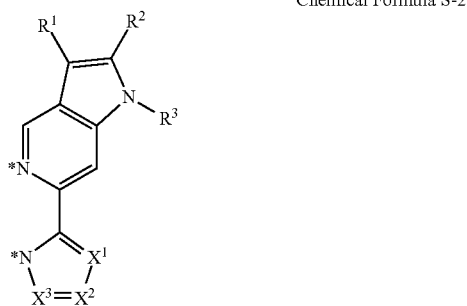

Chemical Formula S-2 wherein, in Chemical Formula S-2,
$X^1$ to $X^3$ are each independently N or CR', provided that at least one of $X^1$ to $X^3$ is N,
$R^1$ to $R^3$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group,
wherein at least two of $R^1$ to $R^3$ are optionally connected to form a fused ring, and
* indicates a binding position to M of Chemical Formula 1.

5. The organometallic complex of claim 1, wherein the cyclometalating ligand is represented by Chemical Formula S-3:

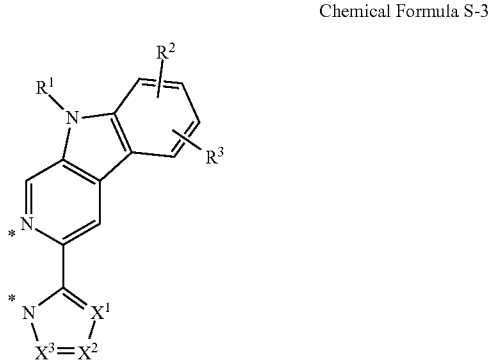

Chemical Formula S-3 wherein, in Chemical Formula S-3,
$X^1$ to $X^3$ are each independently N or CR', provided that at least one of $X^1$ to $X^3$ is N,
$R^1$ to $R^3$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group, and
* indicates a binding position to M of Chemical Formula 1.

6. An organometallic complex represented by Chemical Formula 1,

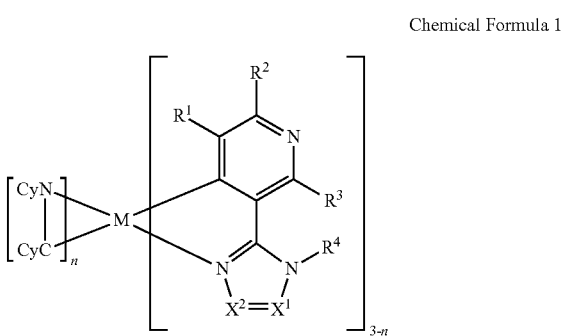

Chemical Formula 1 wherein, in Chemical Formula 1,
M is Ir, Os, Pt, Pb, Re, Ru, or Pd,
$X^1$ and $X^2$ are each independently N or CR',
$R^1$ to $R^4$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group, wherein R³ and R⁴ are optionally connected to form a fused ring,
n is 1 or 2, and
CyN-CyC is a cyclometalating ligand represented by one of chemical formulae:
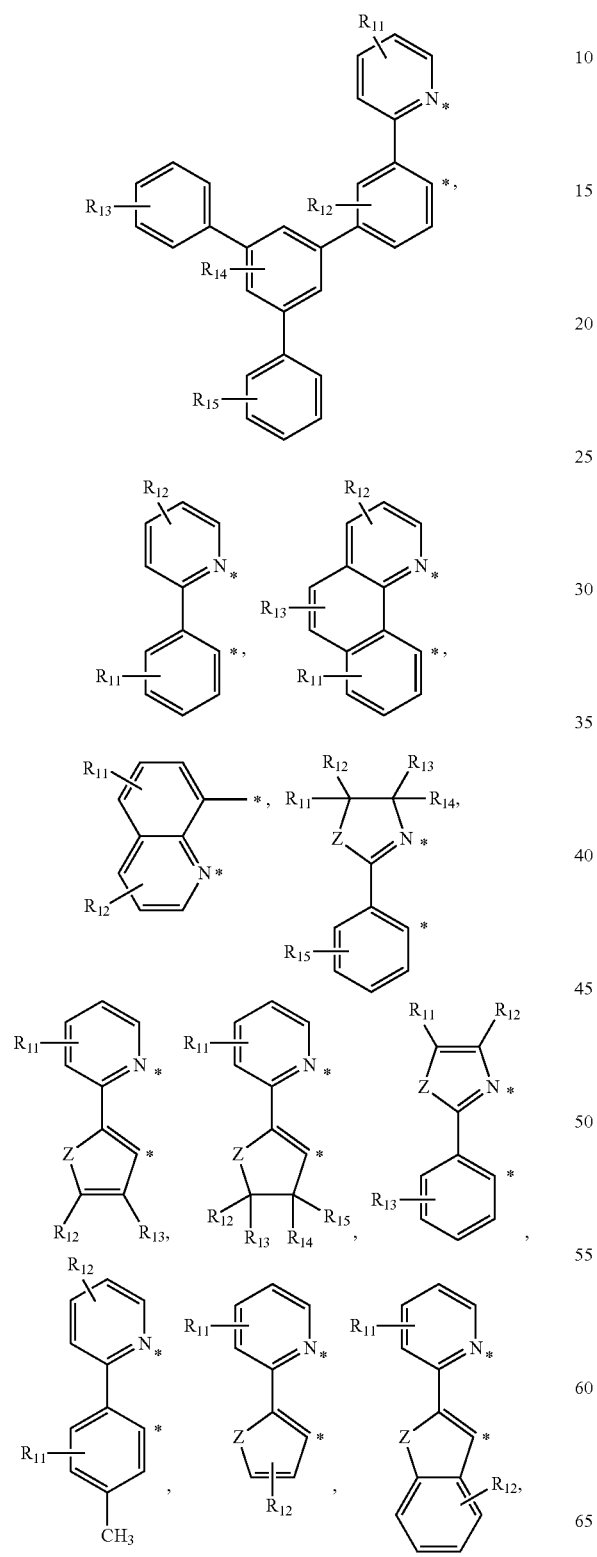
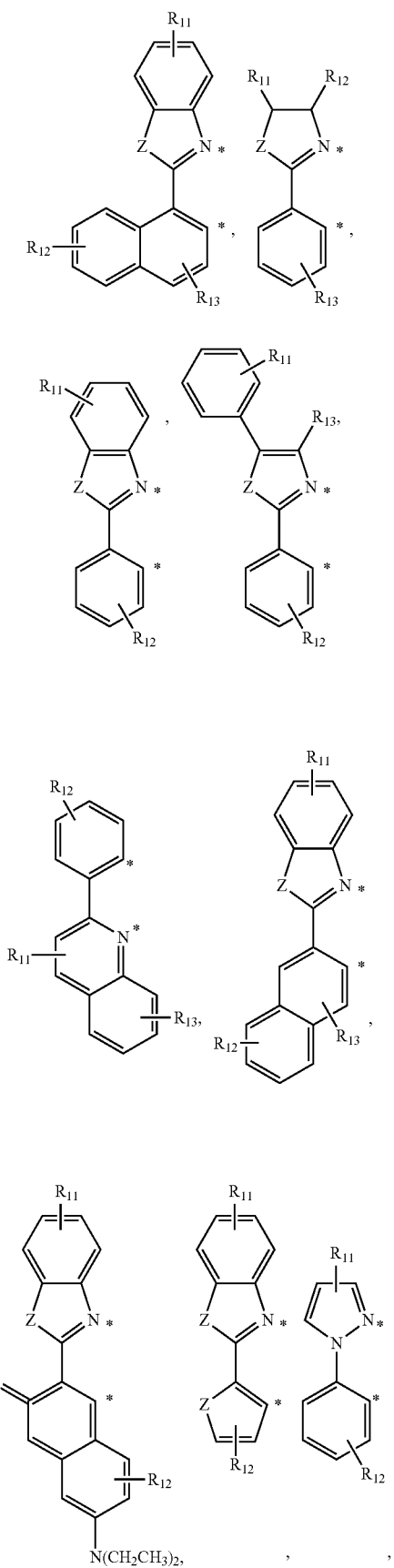

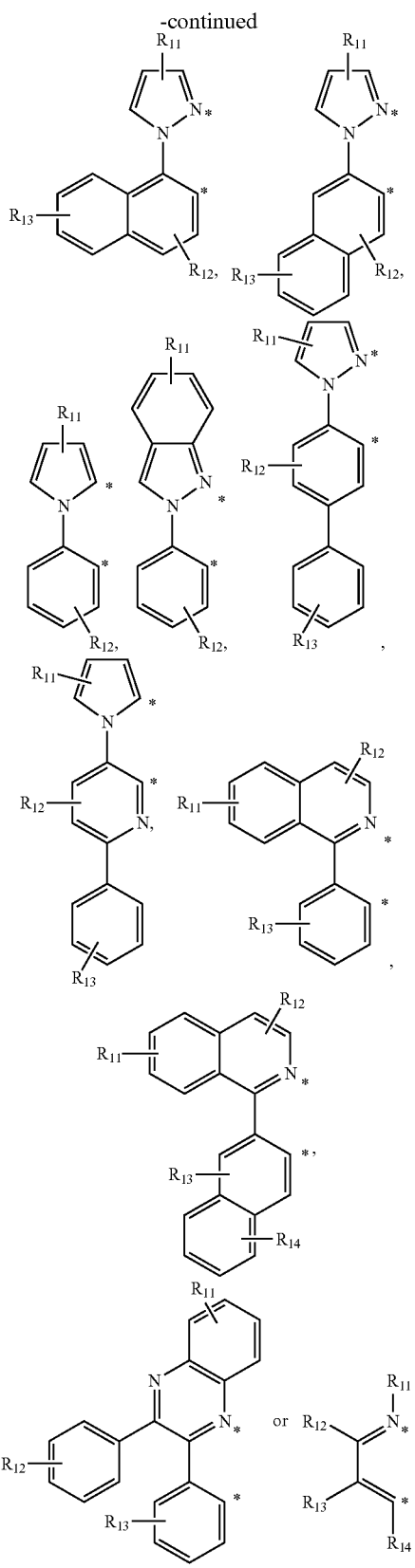

wherein, in the chemical formulae,

R$^{11}$, R$^{12}$, R$^{13}$, R$^{14}$, and R$^{15}$ are each independently a monosubstituted or multisubstituted functional group, and are each independently hydrogen, a halogen, —OR, —N(R)$_2$, —P(R)$_2$, —P(O)(R)$_2$, —P(O)(OR)$_2$, —P(OR)$_2$, —SR, —Si(R)$_3$, —B(R)$_2$, —B(OR)$_2$, —C(O)R, —C(O)OR, —C(O)N(R), —CN, —NO$_2$, —S(O)R, —S(O)$_2$R, —S(O)$_2$(OR), a C1 to C20 alkyl group, or a C6 to C20 aryl group, wherein R is hydrogen, deuterium, a halogen, a substituted or unsubstituted C1 to C20 alkyl group, a substituted or unsubstituted C1 to C10 alkoxy group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C6 to C40 aryl group, a substituted or unsubstituted C7 to C40 arylalkyl group, a substituted or unsubstituted C7 to C40 alkylaryl group, a substituted or unsubstituted C2 to C40 heteroaryl group, or a substituted or unsubstituted C3 to C40 heteroarylalkyl group, the substituents of a group corresponding to CyN of Chemical Formula 1 of claim 1 are connected to one another to form a substituted or unsubstituted 4 to 7 atom fused cyclic group or a substituted or unsubstituted 4 to 7 atom fused heterocyclic group, Z is S, O, or NR$^0$ (wherein R$^0$ is hydrogen or a C1 to C20 alkyl group), and

* indicates a binding position to M of Chemical Formula 1.

7. An organometallic complex represented by Chemical Formula 1,

Chemical Formula 1

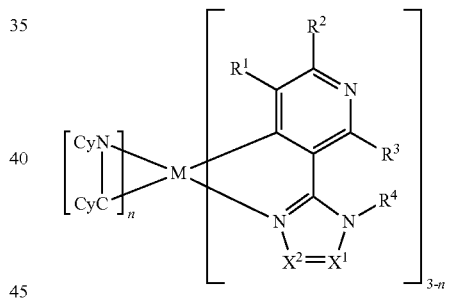

wherein, in Chemical Formula 1,

M is Ir, Os, Pt, Pb, Re, Ru, or Pd,

X$^1$ and X$^2$ are each independently N or CR',

R$^1$ to R$^4$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, SF$_5$, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group, wherein $R^3$ and $R^4$ are optionally connected to form a fused ring, n is 1 or 2, and CyN-CyC is a cyclometalating ligand represented by one of chemical formulae:

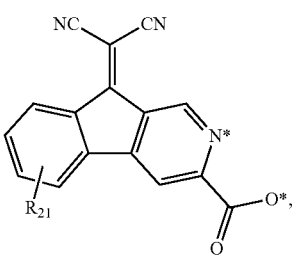

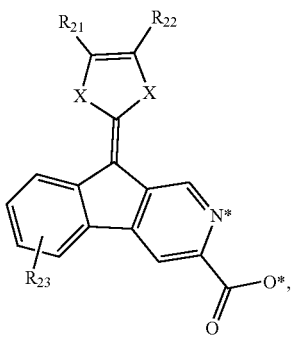

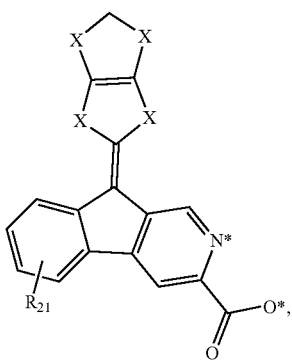

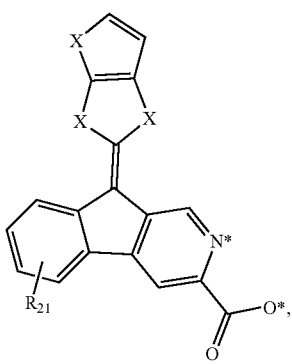

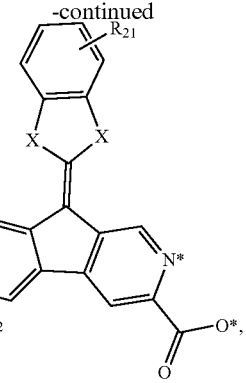

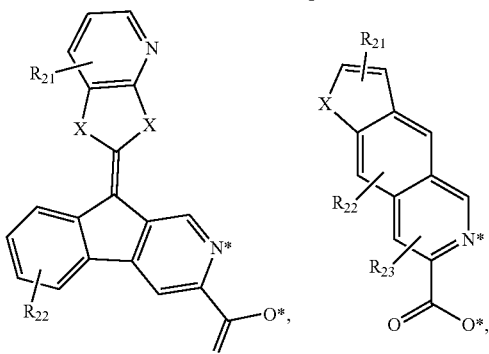

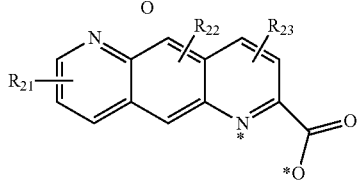

wherein, in the chemical formulae, $R_{21}$, $R_{22}$, and $R_{23}$ are each independently a monosubstituted or multisubstituted functional group, and are each independently hydrogen, a halogen atom, —OR, —N(R)$_2$, —P(R)$_2$, —P(O)(R)$_2$, —P(O)(OR)$_2$, —P(OR)$_2$, —SR, —Si(R)$_3$, —B(R)$_2$, —B(OR)$_2$, —C(O)R, —C(O)OR, —C(O)N(R), —CN, —NO$_2$, —S(O)R, —S(O)$_2$R, —S(O)$_2$(OR), a C1 to C20 alkyl group, or a C6 to C20 aryl group, wherein R is hydrogen, a halogen, a substituted or unsubstituted C1 to C20 alkyl group, a substituted or unsubstituted C1 to C10 alkoxy group, a substituted or unsubstituted C2 to C20 alkenyl group, a substituted or unsubstituted C2 to C20 alkynyl group, a substituted or unsubstituted C1 to C20 heteroalkyl group, a substituted or unsubstituted C6 to C40 aryl group, a substituted or unsubstituted C7 to C40 arylalkyl group, a substituted or unsubstituted C7 to C40 alkylaryl group, a substituted or unsubstituted C2 to C40 heteroaryl group, or a substituted or unsubstituted C3 to C40 heteroarylalkyl group, X is oxygen or sulfur, and

* indicates a binding position to M of Chemical Formula 1.

8. The organometallic complex of claim 1, wherein the M is Ir or Pt.

9. An organometallic complex represented by one of Chemical Formulae A-1, A-2, A-4 to A-19, and A-22 to A-29:

A-1
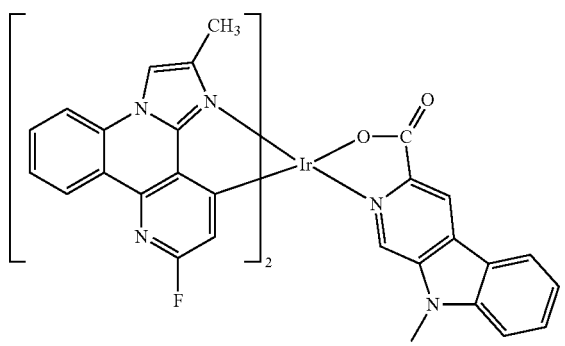
A-2
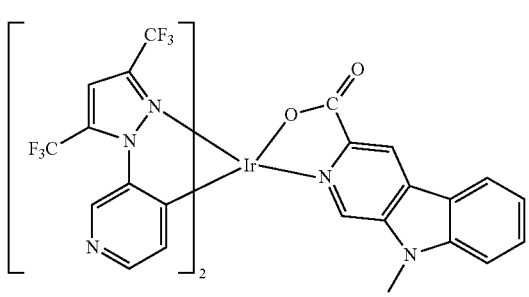
A-4
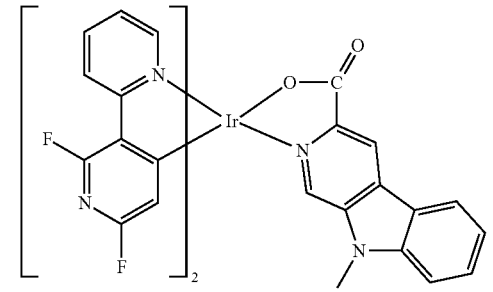
A-5
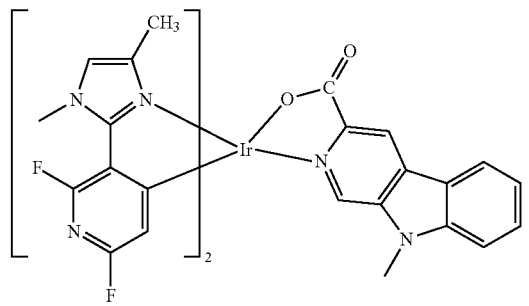
A-6
-continued
A-7
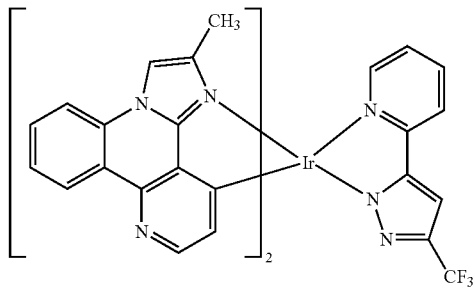
A-8
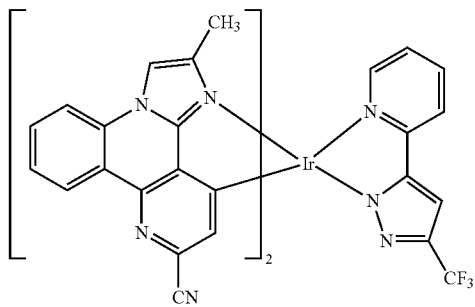
A-9
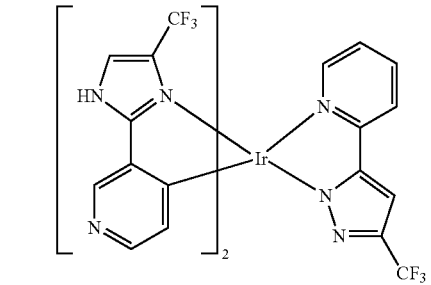
A-10
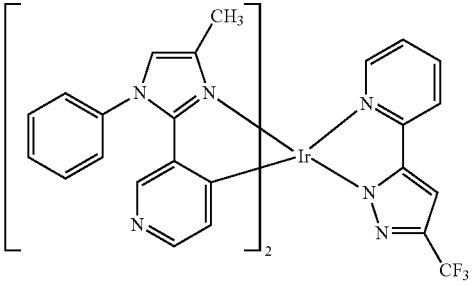
A-11
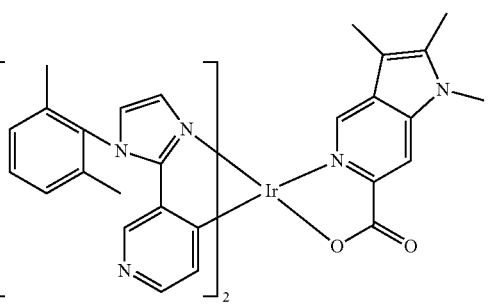

A-12 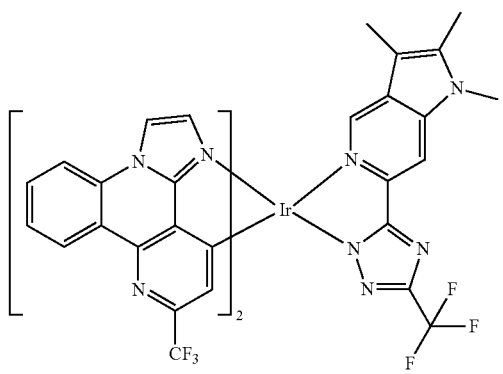
A-13 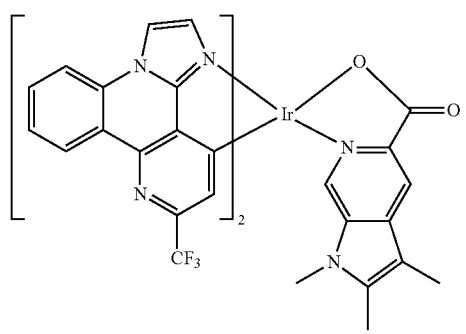
A-14 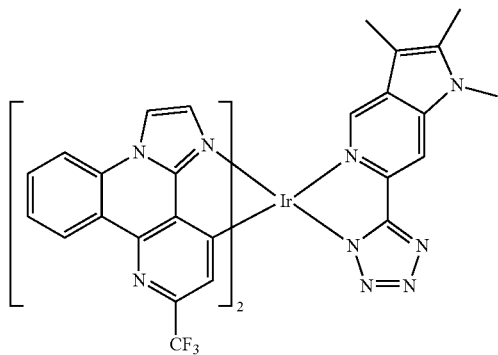
A-15 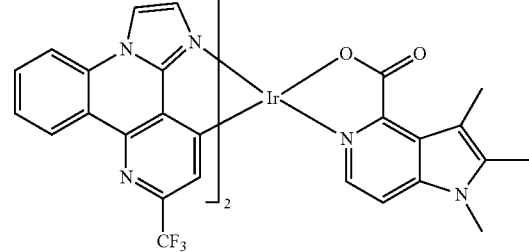
A-16 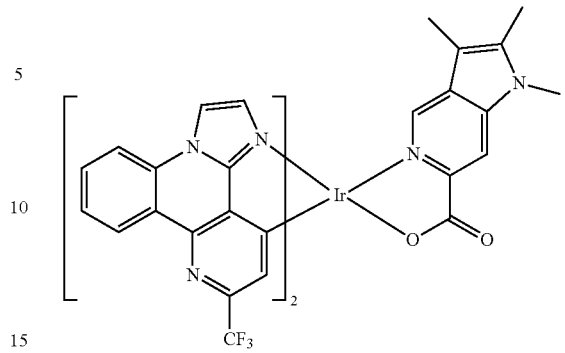
A-17 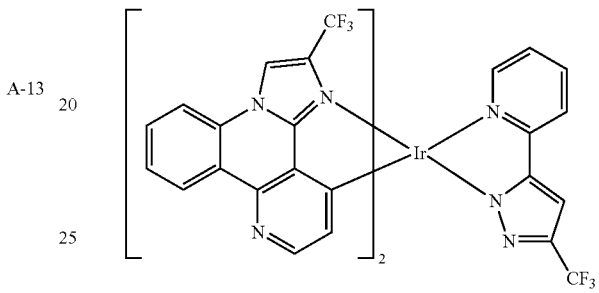
A-18 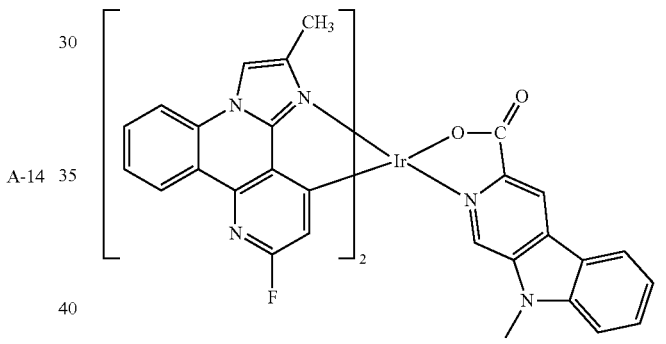
A-19 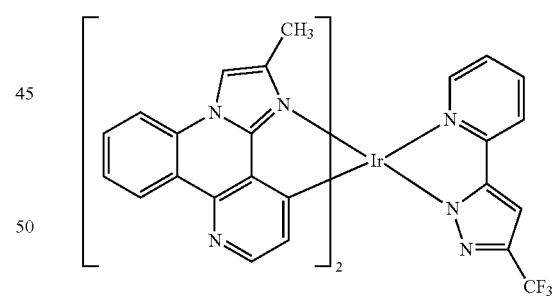
A-22 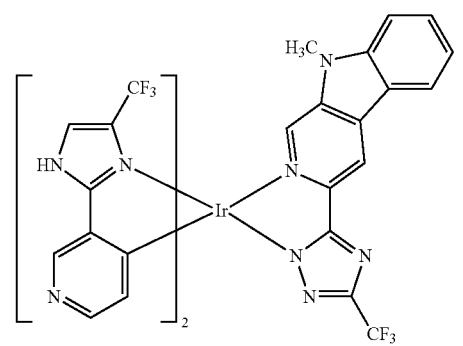

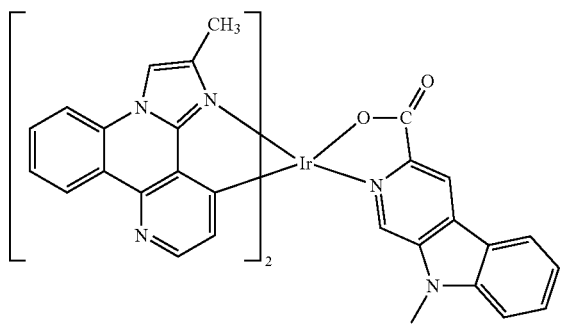

A-23

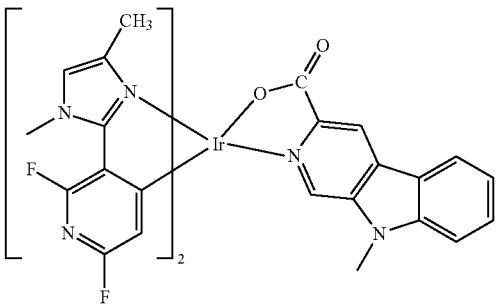

A-24

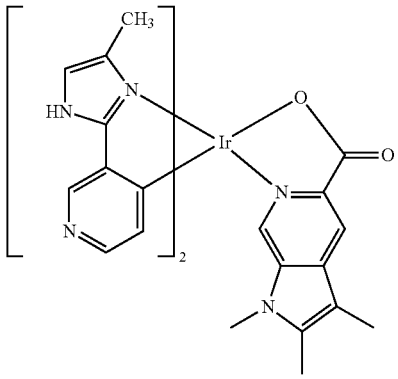

A-25

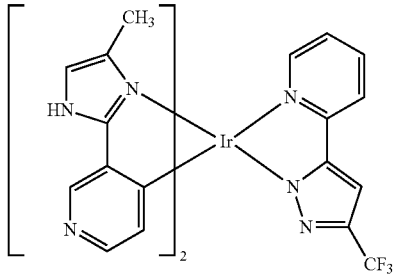

A-26

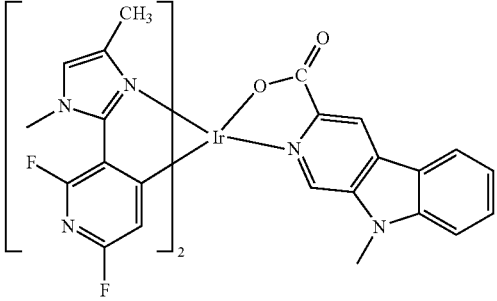

A-27

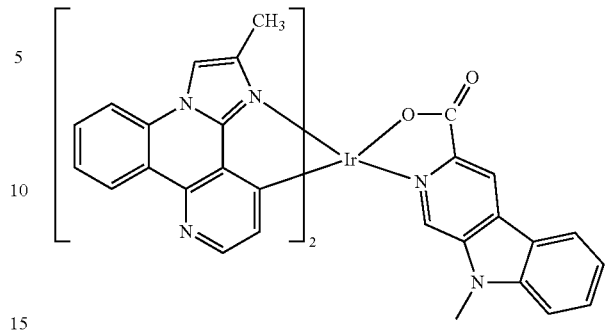

A-28

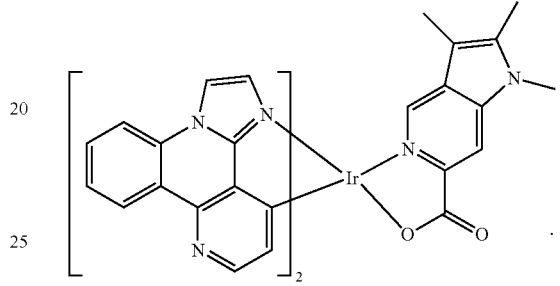

A-29

10. An organic electroluminescent device comprising
a first electrode;
a second electrode; and
an organic layer disposed between the first and second electrodes,
wherein the organic layer comprises the organometallic complex according to claim 1.

11. The organic electroluminescent device of claim 10, wherein the organic layer is an emission layer.

12. The organic electroluminescent device of claim 11, wherein an amount of the organometallic complex is about 1 to about 30 parts by weight based on 100 parts by weight of an emission layer-forming material.

13. A display device comprising the organic electroluminescent device according to claim 10.

14. The display device of claim 13, wherein the organic layer is an emission layer.

15. The display device of claim 13, wherein an amount of the organometallic complex is about 1 to about 30 parts by weight based on 100 parts by weight of an emission layer-forming material.

16. The display device of claim 13, wherein the organometallic complex is represented by Chemical Formula 2:

Chemical Formula 2

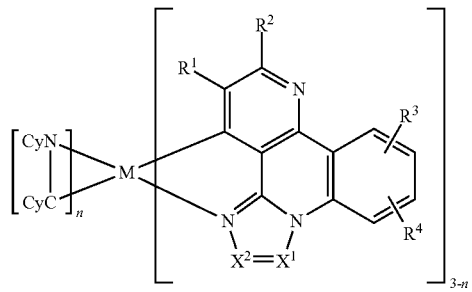

wherein, in Chemical Formula 2,

M is Ir, Os, Pt, Pb, Re, Ru, or Pd,

CyN is a substituted C2 to C60 heterocyclic group wherein nitrogen is bonded to M, or a substituted C3 to C60 heteroaryl group wherein nitrogen is bonded to M, wherein the substituents of CyN are connected to one another to form a substituted or unsubstituted 4 to 7 atom fused cyclic ring or a substituted or unsubstituted 4 to 7 atom fused heterocyclic ring, CyC is a substituted or unsubstituted C3 to C60 heterocyclic group wherein carbon is bonded to M, a substituted or unsubstituted C3 to C60 heterocyclic group wherein nitrogen is bonded to M, a substituted or unsubstituted C3 to C60 heteroaryl group wherein carbon is bonded to M, a substituted or unsubstituted C3 to C60 heteroaryl group wherein nitrogen is bonded to M, CyN-CyC is a cyclometalating ligand bonded to M through nitrogen, oxygen, or carbon, $X^1$ and $X^2$ are each independently N or CR', and $R^1$ to $R^4$ and R' are each independently hydrogen, deuterium, a halogen, a substituted or unsubstituted C1 to C30 alkyl group, a substituted or unsubstituted C1 to C30 alkoxy group, a substituted or unsubstituted C3 to C30 cycloalkyl group, a substituted or unsubstituted C3 to C30 cycloalkoxy group, a substituted or unsubstituted C2 to C30 alkenyl group, a substituted or unsubstituted C2 to C30 alkynyl group, a substituted or unsubstituted C6 to C30 aryl group, a substituted or unsubstituted C6 to C30 aryloxy group, a substituted or unsubstituted C1 to C30 heteroaryl group, a substituted or unsubstituted C1 to C30 heteroaryloxy group, a substituted or unsubstituted C1 to C30 amino group, a substituted or unsubstituted C6 to C30 arylamino group, $SF_5$, a trialkylsilyl group comprising a substituted or unsubstituted C1 to C30 alkyl group, a dialkylarylsilyl group comprising a substituted or unsubstituted C1 to C30 alkyl group and a C6 to C30 aryl group, or a triarylsilyl group comprising a substituted or unsubstituted C6 to C30 aryl group, and n is 1 or 2.

* * * * *